US005871959A

United States Patent [19]
Rong et al.

[11] Patent Number: 5,871,959
[45] Date of Patent: Feb. 16, 1999

[54] METHOD OF PRODUCING HEPATOCYCTE GROWTH FACTOR/SCATTER FACTOR AND RELATED CELL LINES

[75] Inventors: Sing Rong, Frederick, Md.; George Vande Woude, Berryville, Va.; Donna L. Faletto, New Market, Md.; Ilan Tsarfaty, Tel Aviv, Israel; Marianne Oskarsson, Gaithersburg, Md.

[73] Assignee: The United States of America as represented by the Department of Health and Human Services, Washington, D.C.

[21] Appl. No.: 344,710

[22] Filed: Nov. 18, 1994

Related U.S. Application Data

[63] Continuation-in-part of Ser. No. 246,667, May 20, 1994, abandoned, which is a continuation-in-part of Ser. No. 946,061, Sep. 18, 1992, abandoned, which is a continuation-in-part of Ser. No. 642,971, Jan. 18, 1991, Pat. No. 5,648,273, which is a continuation-in-part of Ser. No. 457,556, Dec. 27, 1989, abandoned, and a continuation-in-part of Ser. No. 582,063, Sep. 14, 1990, abandoned.

[51] Int. Cl.$^6$ .............................. C12N 5/00; C12N 15/00; C12N 15/79; C12N 15/73
[52] U.S. Cl. ................. 435/69.1; 435/172.3; 435/360; 435/366; 435/352; 435/320.1; 435/325; 424/93.21
[58] Field of Search .......................... 435/69.4, 69.2, 435/69.3, 69.5, 69.1, 320.1, 240.2, 6; 935/62, 55, 56, 57, 34, 66, 70, 71

[56] References Cited

U.S. PATENT DOCUMENTS 5,004,805  4/1991  Gohda et al. ........................... 530/399

FOREIGN PATENT DOCUMENTS

| 0 456 188 A1 | 11/1991 | European Pat. Off. . |
| WO 91/12272 | 8/1991 | WIPO . |
| WO 92/05184 | 4/1992 | WIPO . |
| WO 92/13097 | 8/1992 | WIPO . |
| WO 93/15754 | 8/1993 | WIPO . |

OTHER PUBLICATIONS

Miyazawa, et al., Molecular Cloning and Sequence Analysis of cDNA for Human Hepatocyte Growth Factor, BBRC, pp. 967–973.

Gherardi, et al., Hepatocytes and Scatter Factor, Nature, 1990, vol. 346, p. 228.

Nakamura, et al. Purification and Subunit Structure of Hepatocyte Growth Factor from Rat Platelets, FEBS, 1987, vol. 224, No. 2, pp. 311–316.

Gherardi, et al., Purification of Scatter Factor, A Fibroblast—Derived Basic Protein That Modulates Epithelial Interactions and Movement, PNAs,1989, vol. 86, pp. 5844–5848.

Zarneger, et al., Identification and Partial Characterization of Receptor Binding Sites For HGF On Rat Hepatocytes, BBRC, vol. 173, No. 3, 1990, pp. 1179–1185.

Vande Woude, Hepatocyte Growth Factor: Mitogen, Motogen, and Morphogen, Japanese Journal Cancer Research, vol. 83, No. 2, 1992.

Graziani, et al., The Tyrosine—Phosphorylated Hepatocyte Growth Factor/Scatter Factor Receptor . . ., JBC, vol. 266, No. 33, 1991, pp. 22087–22090.

Gherardi, et al., Hepatocyte Growth Factor–Scatter Factor . . ., Cancer Cells, vol. 3, No. 6, 1991, pp. 227–232.

Weidner, et al., Scatter Factor: Molecular Characteristics And Effect On The Invasiveness Of Epithelial Cells, JCB, vol. III, 1990, pp. 2097–2108.

Naldini, et al., Scatter Factor and Hepatocyte Growth Factor Are Indistinguishable Ligands For The MET Receptor, EMBO Journal, vol. 10, No. 10 1991, pp. 2867–2878.

Gohda, et al., Purification And Partial Characterization of Hepatocyte Growth Factor From Plasma Of A Patient . . ., J. Clin. Invest, vol. 81, 1988, pp. 414–419.

Nakamura, et al., Molecular Cloning And Express Of Human Hepatocyte Growth Factor, Nature, 1989, vol. 342, pp. 440–443.

Lokker, N.A. et al., "Structure—Function Analysis of Hepatocyte Growth Factor: Identification of Variants That Lack Mitogenic Activity . . .", The EMBO Jour., 11(7) 2503–2510 (1992).

Shima, N. et al., "Tumor Cytotoxic factor/Hepatocyte growth Factor From Human Fibroblasts: Cloning of Its cDNA, Purification . . .", Biochem. and Biophys. Research Comm., 180(2): 1151–1158 (1991).

Blair et al., Science, 218:1122 (1982).
Iyer et al., Cell Growth & Diff., 1(2):87 (1982).
Bottaro et al., Science 251:802 (1991).
Roussell et al., Cell 55: 979–988 (1988).

(List continued on next page.)

Primary Examiner—Jasemine C. Chambers
Assistant Examiner—Karen M. Hauda
Attorney, Agent, or Firm—Needle & Rosenberg, P.C.

[57] ABSTRACT

A method of preventing tumor cell metastasis by inhibiting the binding of hepatocyte growth factor/scatter factor ("HGF/SF") with met proto-oncogene protein is described. A method of producing HGF/SF and a cell line for the production of HGF/SF are also described. The met proto-oncogene tyrosine kinase receptor (Met) and its ligand, hepatocyte growth factor/scatter factor (HGF/SF), ordinarily constitute a paracrine signalling system in which cells of mesenchymal origin produce the ligand, which binds to the receptor that is predominantly expressed in cells of epithelial origin. The method of the present invention disrupts the Met-HGF/SF autocrine signaling that contributes to the tumorigenic process in tumors of mesenchymal origin, such as sarcomas.

12 Claims, 32 Drawing Sheets

OTHER PUBLICATIONS

Sporn et al. *Nature* 313: 745.

Rong et al., *Cell Growth & Diff.* 4:563–569 (1993).

Rong et al., *Mol. & Cell Biol.* 12(11):5152 (1992).

Higashio et al., *Biochem. & Biophys. Res. Comm.*, 170(1):397–404 (1990).

Rosen et al., The Interaction of HGF–SF With Other Cytokines In Tumor Invasion And Angiogensis, Hapatocyte Growth Factor: Scatter Factor and the C–met receptor, eds. Birkhauser Verlag, Base, Switzerland, 1993, pp. 301–310.

Weidner et al., *J. Cell Biology*, 121(1): 145–154 (1993).

Giordano et al., *PNAS (USA)*, 90:649–653 (1993).

Jiang et al., *Br. J. Surg.*, 80:1368–1373 (1993).

Gherardi et al., *Cancer Cells*, 3(6):227–232 (1991).

Rong et al., *Cancer Research*, 1993, 53:5355–5360.

Tsarfaty et al., *Science*, 263:98–101 (1994).

Rong et al., *PNAS (USA)*, 91:4731–4735 (1994).

| TRANSFECTED GENES* | | MICE WITH TUMORS/NO.TESTED | LATENCY (WEEKS) | TRANSFORMED PHENOTYPE | COLONY FORMATION IN SOFT AGAR |
|---|---|---|---|---|---|
| met^mu | xxxxxxxxxxxxxxxxxxxxxxxx (TM →) | 11/12 | 3-5 | + | + |
| met^hu | xxxxxxxxxxxxx------------ | 0/7 | - | - | - |
| met^mu–met^hu (PvuII) | ------------xxxxxxxxxxxxx | 6/7 | 6-7 | + | + |
| met^hu–met^mu (PvuII) | ------------xxxxxxxxxxxxx | 1/11 | 5 | - | ND^b |
| met^mu–met^mu (PvuII) +HGF^hu | ------------xxxxxxxxxxxxx | 6/7 | 3-6 | ± | ND^b |
| met^hu–met^mu (NdeI) | ------------xxxxxxxxxxxxx | 11/12 | 3-5 | ± | ND^b |
| met^mu–met^hu (NdeI) | xxxxxxxx------------ | 0/10 | - | - | - |

FIG.5

```
HUMAN  501 YTLVITGKKITKIPLNGLGCCRHFQSCSQCLSAPPFVQCGWCHDKCVRSEE 550
            ||||:|||||||||||||||||:||||||||||||||:|||||::||::|
MOUSE  500 YTLVVTGKKITKIPLNGLGCCHFQSCSQCLSAPYFIQCGWCHNQCVRFDE 549

551 CLSGTWQQICLPAIYKVFPNSAPLEGGTRLTICGWDFGFRRNNKFDLKK  600
           |||||||||:||||:|||||:|||||||:|||||||||||:||||||:|
       550 CPSGTWQEICLPAVYKVFPTSAPLEGGTVLTICGWDFGFRKNNKFDLRK  599

601 TRVLLGNESCTLTLSESTMNTLKCTVGPAMNKHFNMSIIISNGHGTTQYS 650
           |:|||||||||||||||||||||||||||+|||+||||||++||||||||
       600 TKVLLGNESCTLTLSESTNTLKCTVGPAMSEHFNVSVIISNSRETTQYS  649

651 TFSYVDPVITSISPKYGPMAGGTLLTLLTGNYLNSGNSRHISIGGKTCTLK 700
           :|||||||||||||||:|||:||||||||||||||||||||||||||||||
       650 AFSYVDPVITSISPRYGPQAGGTLLTLLTGKYLNSGNSRHISIGGKTCTLK 699

701 SVSNSILECYTPAQTISTEFAVKLKIDLANRETSIFSYREDPIVYEIHPT  750
           |||:|||||||||||||:|:||:||||||||||||||:||||||:|||||
       700 SVSDSILECYTPAQTISDEFPVKLKIDLANRETSSFSYREDPVVYEIHPT  749

751 KSFISSGGSTITGVGKNLNSVSVPRMVINVHEAGRNFTVACQHRSNSEII  850
           |||| |||||||| |:|||||||| ||| +||||+| ||||||||||||||
       750 KSFI.SGGSTITGIGKTLNSVSLPKLVIDVHEVGVNYTVACQHRSNSEII  849
```

A. REACTIVITY OF MET TO DIFFERENT ANTIBODIES

| | C23 . 19S | 260 | 1242 | 1243 |
|---|---|---|---|---|
| MET$^{hu}$ (p170, p140) | +++ | − | + | − |
| MET$^{mu}$ (p170, p140) | − | +++ | − | ++ |

B. IN VITRO INVASIVE ASSAY OF NIH/3T3 TRANSFECTED CELLS [a]

| TRANSFECTED GENE | FILTER INVASION | 1242 [c] | 1243 [a] | 1242 + PEPTIDE [d] |
|---|---|---|---|---|
| neo | − | ND [a] | ND | ND |
| neo$^r$, met$^{hu}$ | ± [b] | ± [b] | ND | + [b] |
| neo$^r$, met$^{mu}$ | + | ND | ++ | ND |
| neo$^r$, met$^{hu}$, HGH$^{hu}$ | + | + | ND | ND |
| tpr−met | + | + | ND | ND |

FIG. 8

A. IN VIVO MET-MEDIATED LUNG METASTASIS

| TRANSFECTED GENES | #WITH METASTASIS / # TESTED | LATENCY (WEEKS) |
|---|---|---|
| neo$^r$, tpr-met | 3/4 | 3-4 |
| neo$^r$, met$^{mu}$ | 6/7 | 6-7 |
| neo$^r$, met$^{hu}$ | 0/4 | — |
| neo$^r$, met$^{hu}$, HGF$^{hu}$ (1°) | 7/10 | 3-6 |

B. IN VIVO MET-MEDIATED SPONTANEOUS METASTASIS

| TRANSFECTED GENES | INJECTION SITE | #METASTASIS/ #TESTED | TARGET ORGAN | LATENCY (WEEKS) |
|---|---|---|---|---|
| neo$^r$, tpr-met | S.Q | 1/3 | LUNG | 5 |
| neo$^r$, met$^{mu}$ | K.C. | 2/2 | INTESTINE, DIAPHRAGM | 4 |
| neo$^r$, met$^{hu}$, HGF$^{hu}$ | K.C. | 1/1 | SPLEEN, STOMACH | 6 |

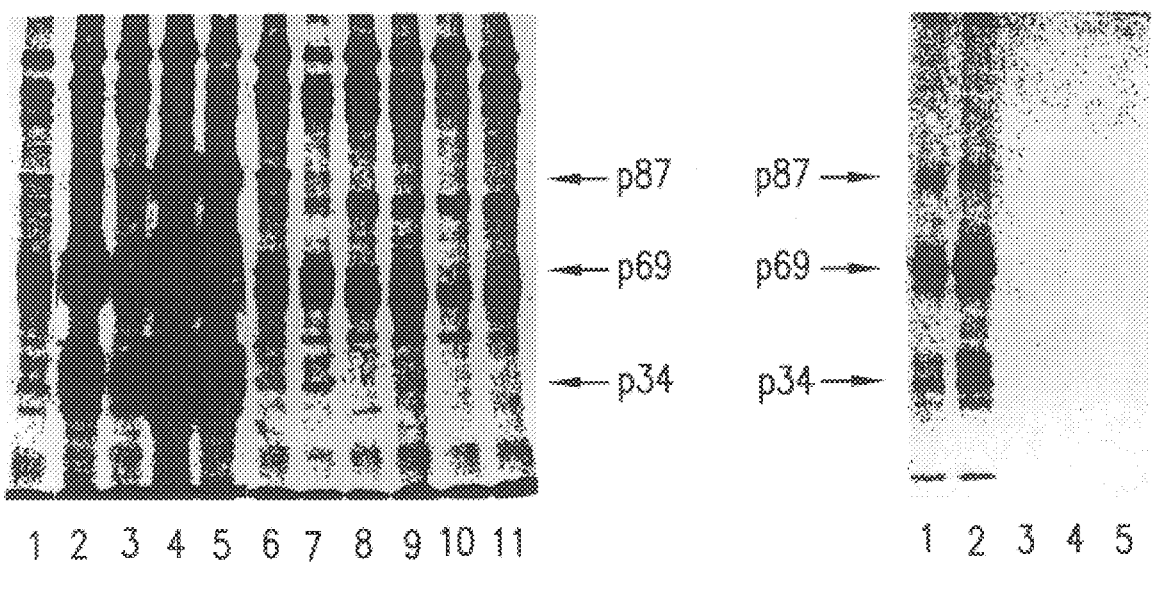

Met AND HGF/SF EXPRESSION IN HUMAN FIBROBLAST AND SARCOMA CELL LINES

| | Met[a] | met[b] | HGF/SF[c] | SCATTER ACTIVITY[d] | P-Tyr-Met[e] |
|---|---|---|---|---|---|
| 1. HUMAN DIPLOID FIBROBLAST | | | | | |
| HEL 299 (FETAL LUNG) | + | + | ++++ | ++++ | − |
| HEMS (FETAL MUSCLE) | ++ | +++ | +++ | +++ | + |
| Hs68 (NEWBORN FIBROBLAST) | ++ | ++ | ++++ | + | − |
| MALME-3 (SKIN FIBROBLAST) | + | ND | ++++ | + | ND |
| 2. FIBROSARCOMA | | | | | |
| 8387 | ++++ | ++++ | ++ | + | +++ |
| HT1080 | ++++ | +++ | + | + | +++ |
| Hs913T | ++++ | ++ | ++++ | + | ++++ |
| SW684 | ++++ | ND | ++ | − | +++ |
| 3. OSTEOGENIC SARCOMA | | | | | |
| HOS | +++ | + | − | − | + |
| SAOS-2 | +++ | ++++ | + | + | ++ |
| U-205 | +++ | + | − | − | ++ |
| 4. CHONDROSARCOMA | | | | | |
| SW1353 | ++ | ND | − | ND | ND |
| 5. RHABDOMYOSARCOMA | | | | | |
| RD | +++ | ++ | − | + | ++ |
| RD-1 | ++ | + | + | + | − |
| A204 | − | ND | − | ND | − |
| A673 | + | ND | − | − | + |
| Hs729 | +++ | ND | + | + | +++ |

FIG.21A

| | Met[a] | met[b] | HGF/SF[c] | SCATTER ACTIVITY[d] | P-Tyr-Met[e] |
|---|---|---|---|---|---|
| 6. LEIOMYOSARCOMA | | | | | |
| SK-LMS-1 | ++++ | ND | + | + | ++++ |
| SK-UT-1B | + | ND | − | + | +++ |
| 7. LIPOSARCOMA | | | | | |
| SW872 | +++ | +++ | − | ND | − |
| 8. MESODERMAL TUMOR | | | | | |
| SK-UT-1 | ++++ | ND | − | − | +++ |
| 9. SYNOVIAL SARCOMA | | | | | |
| SW982 | + | ND | +++ | − | + |
| 10. MELANOMA | | | | | |
| MALME-3M | +++ | ND | − | − | +++ |
| WM115 | + | ND | + | − | + |
| WM266-4 | + | ND | − | − | − |

FIG.21B

| IN VITRO MOTILITY INVASIVENESS ASSAY | | | | | | | |
|---|---|---|---|---|---|---|---|
| | HUMAN HGF/SF (UNITS/ml) | | | | MOUSE HGF/SF (UNITS/ml) | | |
| CELLS | 0 | 5U | 30U | 200U | 5U | 30U | 200U |
| Neo$^r$ | − | − | − | − | − | − | − |
| MT | − | +++++ | ++++ | ++ | + | ++ | − |
| Met$^{mu}$ | +/− | +++ | ++ | + | + | ++++ | + |
| HMH | +/− | +/− | + | ND | − | − | ND |
| HMH 1° EXPLANT* | ++ | + | + | ND | + | + | ND |
| Tpr-Met | ++ | ND | + | ND | ND | ND | ND |

FIG.22

Met-MEDIATED EXPERIMENTAL LUNG METASTASIS

A. ATHYMIC MICE

| CELLS | METASTASIS/TOTAL | LATENCY (WEEKS) |
|---|---|---|
| Neo$^r$ | 2/11* | 10 |
| MT | 1/6 | 7 |
| Tpr-Met | 4/4 | 3 |
| Met$^{mu}$ | 6/6 | 6-7 |
| HMH | 2/6 | 7 |
|    HMH 1° EXPLANT | 2/3 | 3 |
|    HMH 2° EXPLANT | 4/5 | 2-3 |

B. EXPERIMENTAL METASTASIS IN IMMUNE COMPETENT TRIPLE DEFICIENCY MICE (TDM)

| CELLS | METASTASIS/TOTAL Balb/c | NFS | TDM |
|---|---|---|---|
| Neo$^r$ | 0/3 | 0/2 | 0/2 |
| Tpr-Met | 2/3 (3)** | 2/3 (7) | 2/2 (2) |
| Met$^{mu}$ | 0/6 | 0/6 | 2/3 (8) |
| HMH | 0/3 | 0/3 | 1/3 (8) |

FIG.23

Met-MEDIATED SPONTANEOUS METASTASIS IN ATHYMIC MICE

A. SUBCUTANEOUSLY INJECTED

| CELLS* | METASTASIS/TOTAL | ORGANS | CELLS INJECTED | LATENCY (WEEKS)** |
|---|---|---|---|---|
| Neo$^r$ | 0/4 | – | $10^6$ | |
| MT | 0/11 | – | $10^6$ | |
| Tpr-Met | 2/3 | LUNG | $10^6$ | 6 |
| Met$^{mu}$ | 1/9 | LUNG | $10^6$ | |
| | 1/3 | LUNG | $3 \times 10^5$ | 10 |
| | 0/3 | – | $10^5$ | |
| Met$^{mu}$ 1° EXPLANT | 2/6 | LUNG | $10^6$ | 5 |
| | 3/3 | LUNG | $3 \times 10^5$ | 6-7 |
| | 2/3 | LUNG/SALIVARY GLAND/ RETROPERITONEUM | $10^5$ | |
| HMH | 0/8 | – | $10^6$ | |
| | 0/3 | – | $3 \times 10^5$ | |
| | 0/2 | – | $10^5$ | |
| HMH 1° EXPLANT | 2/7 | LUNG | $10^6$ | 6-9 |
| | 1/2 | LUNG | $3 \times 10^5$ | 9 |
| | 2/3 | LUNG/DIAPHRAGM HEART | $10^5$ | 5-8 |
| ras | 2/3 | LUNG | $10^6$ | 4-5 |
| src | 1/3 | LUNG | $10^6$ | 2.5 |

FIG.24A

B. MAMMARY FAT PAD INJECTION

| CELLS | METASTASIS/TOTAL | ORGANS | CELLS INJECTED | LATENCTY (WEEKS) |
|---|---|---|---|---|
| Neo$^r$ | 0/5 | – | $4 \times 10^5$ | 10 |
| Tpr-Met | 3/4 | LUNG | $4 \times 10^5$ | 3-4 |
| Met$^{mu}$ | 1/5 | LUNG | $4 \times 10^5$ | 6 |
| Met$^{mu}$ 1° EXPLANT | 1/5 | LUNG | $4 \times 10^5$ | 3-4 |
| HMH | 0/5 | – | $4 \times 10^5$ | |
| HMH 1° EXPLANT | 2/4 | LUNG | $4 \times 10^5$ | 1-3 |
| HMH 3° EXPLANT | 3/4 | LUNG | $4 \times 10^5$ | 3 |

FIG.24B

METHOD OF PRODUCING HEPATOCYCTE GROWTH FACTOR/SCATTER FACTOR AND RELATED CELL LINES

BACKGROUND OF THE INVENTION

This application is a continuation-in-part of application Ser. No. 08/246,667, filed May 20, 1994, now abandoned, which is a continuation-in-part of application Ser. No. 07/946,061, filed Sep. 18, 1992, now abandoned, which is a continuation-in-part of application Ser. No. 07/642,971, filed Jan. 18, 1991, patented, U.S. Pat. No. 5,648,273, which is a continuation-in-part of application Ser. No. 07/457,556, filed Dec. 27, 1989, now abandoned, and a CIP of application Ser. No. 07/582,063, filed Sep. 14, 1990, now abandoned. The entire contents of these applications are hereby incorporated by reference.

BACKGROUND OF THE INVENTION

Hepatocyte growth factor (HGF) was first purified from human and rabbit plasma and rat platelets on the basis of its ability to stimulate mitogenesis of rat hepatocytes. (E. Gohda et al., *J. Clin. Invest* 81: 414 (1988); R. Zarnegar and G. Michalopoulos, *Cancer Res.* 49: 3314 (1989); T. Nakamura et al. *FEBS Lett.* 224: 311 (1987)). Thus, HGF may act as a humoral factor promoting liver regeneration after partial hepatectomy or liver injury. (E. H. Gohda et al., *J. Clin. Invest.* 81: 414–419 (1988); G. K. Michalopoulos, *FASEB J.* 4: 176 (1990)). The same factor was purified from human fibroblast culture medium and shown to act on melanocytes and a variety of epithelial and endothelial cells. (T. Igawa et al., *BBRC* 174: 831–838 (1991); M. Kan et al., *BBRC* 174: 331–337 (1991) and J. S. Rubin et al., *Proc. Nat'l. Acad. Sci. U.S.A.* 88: 415 (1990)). Together with evidence of HGF expression in several organs (J. S. Rubin et al., *Proc. Nat'l. Acad. Sci. U.S.A.* 88: 415 (1990); K. Tashiro et al. *Proc. Nat'l. Acad. Sci. U.S.A.* 87: 3200 (1990); R. Zarnegar et al., *Proc. Nat'l. Acad. Sci. U.S.A.* 87: 1252 (1990); T. Kinoshita et al., *Biochem. Biophys. Res. Comm.* 165: 1229 (1989)), these findings indicate that HGF may also act as a paracrine mediator of proliferation for a broad spectrum of cell types. Molecular cloning of HGF revealed a remarkable structural homology to plasminogen and related serine proteases (J. S. Rubin et al., *Proc. Nat'l. Acad. Sci. U.S.A.* 88: 415 (1990); T. Nakamura et al., *Nature* 342: 440 (1989); K. Miyazawa et al., *Biophys. Res. Comm.* 163: 967 (1989)). Recent evidence that HGF induces rapid tyrosine phosphorylation of proteins in intact target cells suggests that a tyrosine kinase receptor mediates its mitogenic signal (J. S. Rubin et al., *Proc. Nat'l. Acad. Sci. U.S.A.* 88: 415 (1990)).

HGF is structurally related to the family of serine proteases that includes plasminogen, prothrombin, urokinase, and tissue plasminogen activator (J. S. Rubin et al., *Proc. Nat'l. Acad. Sci. U.S.A.* 88: 415 (1990); T. Nakamura et al., *Nature* 342: 440 (1989)). For instance, HGF structurally resembles plasminogen in that it possesses characteristic kringle domains (Patthy et al. *FEBS Lett.* 171: 131 (1984)) and a serine protease domain (Miyazawa et al., *Biochem. Biophys. Res. Commun.* 163: 967 (1989); Nakamura et al., *Nature* 342: 440–43 (1989)). As defined in the present invention, HGF includes a growth factor previously characterized as a broad-spectrum mitogen called plasminogen-like growth factor (PLGF), the subject matter of U.S. application Ser. No. 07/582,063. Several proteases, including members of the serine protease family, stimulate DNA synthesis presumably through a proteolytic mechanism similar to tryptic activation of the insulin receptor. (S. E. Shoelson et al. *J. Biol. Chem.* 263: 4852 (1988)). Only urokinase has been found to associate with a specific cell-surface receptor, which itself bears no homology to any known tyrosine kinase receptors (A. L. Roldan et al., *EMBO J.* 9: 467 (1990)).

Scatter factor (SF) originally had been considered to be related to but different from HGF, SF being associated with cell motogenicity (motility), and HGF being associated with cell mitogenicity (growth). However, recent work has demonstrated that SF and HGF are, in fact, the same protein having the identical amino acid sequence, the same receptor which is the protein encoded by the c-met proto-oncogene, and same biochemical affect (E. Gherardi et al., *Nature* 346: 228 (1990); K. M. Weidner et al., *PNAS* 88: 7001–7005 (1991); M. Bhargava et al., *Cell Growth & Diffn.* 3(1): 11–20 (1992); Naldini et al., *EMBO J.* 10(10): 2867–78 (1991); E. Gherardi and M. Stoke, *Cancer Cells* 3: (6): 227–32 (1991) and Graziani et al., *J. Biol. Chem.* (*U.S.A.*) 266 (33): 22087–90 (1991)). Thus, HGF and SF are now referred to collectively as "HGF/SF."

Various sources of human HGF have been identified (Nakamura, T., *Progress in Growth Factor Research,* 3: 67–86 (1992)) and it has been shown that the gene product can be overexpressed when transfected into Cos cells or by baculovirus host systems. (Nakamura et al., *Nature* 342:440–43 (1989); Cooper, et al., *The EMBO J.,* 5(10): 2623–2628 (1986)). A mammalian cell line continuously shedding large amounts of human HGF/SF has yet to be identified.

The subject matter of U.S. Ser. No. 07/642,971, incorporated by reference above, describes a complex comprising HGF/SF and met proto-oncogene protein ("Met"), and identifies Met as the receptor for HGF/SF. The met proto-oncogene protein is a member of the tyrosine kinase growth factor receptor family. Knowledge of this receptor/ligand relationship facilitates the study of proliferative disorders and tumorigenicity in which expression of these molecules may play an important role. Additionally, identification of the met proto-oncogene receptor HGF/SF complex provides a means for identifying tissues other than liver tissue affected by factor binding.

Met and HGF/SF ordinarily constitute a paracrine signalling system wherein cells of mesenchymal origin produce HGF/SF and the ligand subsequently binds to the Met receptor, which is predominantly expressed in cells of epithelial origin. Surprisingly, Applicants have discovered that mouse NIH/3T3 fibroblasts that overexpress Met can induce tumor formation in nude mice via an autocrine mechanism due to the interaction between recombinant Met and endogenously-produced HGF/SF. (S. Rong et al. *Mol. Cell Biol.* 12: 5152 (1992). In addition, applicants have shown these cells to be metastatic. (S. Rong et al., *Cell Growth & Diff.* 4: 563 (1993); S. Rong et al., *PNAS* 91: 4731–35 (1994)). Moreover, Applicants' studies have revealed that most human tumors and tumor cell lines of mesenchymal origin inappropriately express Met and/or HGF, suggesting that Met plays a role in sarcomagenesis and that both autocrine and paracrine modes of stimulation can occur in human primary tumors. Thus, Applicants' discoveries indicate that Met-HGF/SF autocrine and/or paracrine signaling contributes to the tumorigenic process in human tumors of mesenchymal origin, such as sarcomas.

SUMMARY OF THE INVENTION

Accordingly, the present invention involves a method for inhibiting tumor metastasis based upon the recognition that HGF and SF are the same protein and that tumor cell metastasis, therefore, may be prevented by treating a tumor-bearing mammal with a medicament containing a tumor metastasis-inhibiting amount of a substance that prevents the binding of HGF/SF with its receptor.

In another embodiment, the invention relates to a method of preventing the further development of a tumor of mesenchymal origin comprising administering to a mesenchymal tumor-bearing subject a medicament containing a tumorigenesis inhibitory amount of a substance that prevents HGF/SF from binding with Met.

A substance which inhibits binding of HGF/SF with Met may be an HGF/SF variant, HGF/SF mimetic, or antibody or antibody fragment against HGF/SF, which prevents HGF/SF from binding with Met. Binding may also be inhibited by a Met variant, Met mimetic and antibody or antibody fragment against Met, which similarly prevents HGF/SF-Met binding.

Furthermore, in view of need for a continuously producing source of large quantities of HGF/SF, applicants have discovered and describe herein that transfected cell lines which can express unexpectedly high levels of HGF/SF by recombinant methods. Thus, one embodiment of the invention relates to a method of producing HGF/SF comprising the steps of:

(a) transfecting eukaryotic cells with DNA encoding HGF/SF$^{hu}$ and Met$^{hu}$;

(b) introducing cells transfected in accordance with step (a) into a mammal, thereby generating a primary tumor;

(c) explanting and propagating cells of the primary tumor in vitro;

(d) selecting those cells propagated in accordance with step (c) which express high levels of HGF/SF$^{hu}$ and high levels of Met$^{hu}$;

(e) introducing cells selected in accordance with step (d) into a mammal, thereby producing a secondary tumor;

(f) explanting and propagating cells of the secondary tumor in vitro; and (g) obtaining HGF/SF$^{hu}$ produced by the cells of step (f).

Yet another embodiment of the invention relates to a cell line co-transfected with a first DNA vector comprising, in operable linkage, a promoter derived from a long terminal repeat of a retrovirus, DNA encoding the entire coding domain of human Met and a polyadenylation signal and a second DNA vector comprising, in operable linkage, a promoter derived from a long terminal repeat of a retrovirus, DNA encoding human HGF/SF and a polyadenylation signal.

Yet another embodiment is the use of Met as a clinically relevant molecular marker for human mesenchymal tumor diagnosis and prognosis. Another embodiment is the use of inhibitors of tyrosine kinase and receptor-ligand interactions or Met specific neutralizing antibodies for possible inhibiting tumor cell metastasis. Another embodiment relates to a method of growing tumors in athymic nude mice.

BRIEF DESCRIPTION OF THE DRAWINGS

The file of this patent contains at least one drawing executed in color.

FIG. 5 shows that the extracellular domain of Met$^{mu}$ confers transforming potential onto Met$^{hu}$ (line 3 compared to line 2) and the Met$^{hu}$ extracellular domain is only transforming when co-transfected with HGF$^{hu}$ (compare lines 4 to 5). Furthermore, the last two lines delineate the region of met$^{mu}$ between the NdeI-PvuII sites as a region conferring transforming potential onto Met$^{hu}$ (compare line 6 to line 4). That is, in order to further define the extracellular domain and to identify the sequence which is involved in HGF/SF ligand binding, applicants made chimeric mouse human met cDNA constructs, transfected them into NIH/3T3 cells and tested their tumorigenicity in nude mice. These results indicate that the region from NdeI to PvuII restriction sites is important for the tumorigenicity. To confirm this result, applicants made a met cDNA construct with only NdeI-PvuII region from mouse met. This construct, when expressed in NIH/3T3 cells is tumorigenic, whereas human met by itself is not. This indicates that this region allows high affinity binding of the receptor and that the region from NdeI to PvuII is involved in ligand binding, either directly or indirectly. The reciprocal construct, mouse met cDNA with only NdeI-PvuII region from human met, is also only part of the ligand-binding site of the receptor, since loss of activity of the chimera would be expected if the mouse ligand binding is restricted to this region.

FIG. 7 depicts the reactivity of human versus mouse Met to the human (C28, 19S, 1242) and mouse (260, 1243) specific antibodies (part A). Part B demonstrates that when mouse met cDNA is transfected into NIH/3T3 cells (which express HGF/SF$^{mu}$, endogenously) the cells are invasive in a Boyden chamber assay. (Albini et al. Cancer Res. 47: 3239–3245 (1987)). That is, the cells move across a filter coated with matrigel (a basement membrane-like compound). Cells transfected with the oncogenic form of met (tpr-met) are also highly invasive in this assay. For cells to invade across the filter, they must not only be motile, but must be able to degrade basement membrane components (and thus secrete enzymes such as collagenase or plasminogenase). Met$^{hu}$ transfectants (line 2) are not invasive in the absence of human ligand, HGF/SF$^{hu}$, but are invasive when conditioned media from the HGF producer cell line is added. On the other hand, cotransfectants of met$^{hu}$ and HGF/SF$^{hu}$ (line 4) are invasive in this assay.

The second column on this figure shows that 1242 antibody to human Met within the domain described above inhibits filter invasion of the met$^{hu}$ transfectants, co-cultured with conditioned media containing HGF/SF$^{hu}$. The last column shows that this inhibition is blocked in the presence of competing peptide. On the other hand, the invasive capacity of cotransfectants producing Met$^{hu}$ and HGF$^{hu}$ (line 4) is not blocked by the 1242 antibody, suggesting internal, intracellular autocrine activation of receptor by co-produced HGF/SF ligand.

Lastly, this figure shows that 1243 antibody did not block invasion of the filter by met$^{mu}$ transfectants (line 3, column 3).

FIG. 8 shows in vivo metastasis data showing that just as met$^{mu}$ and tpr-met transfectants are tumorigenic in vivo (FIG. 5), these cells are also metastatic in several types of assays (panels A and B). Furthermore, Met$^{hu}$ (panel A) is not metastatic in vivo unless cotransfected with HGF$^{hu}$ cDNA.

Figure 9A:
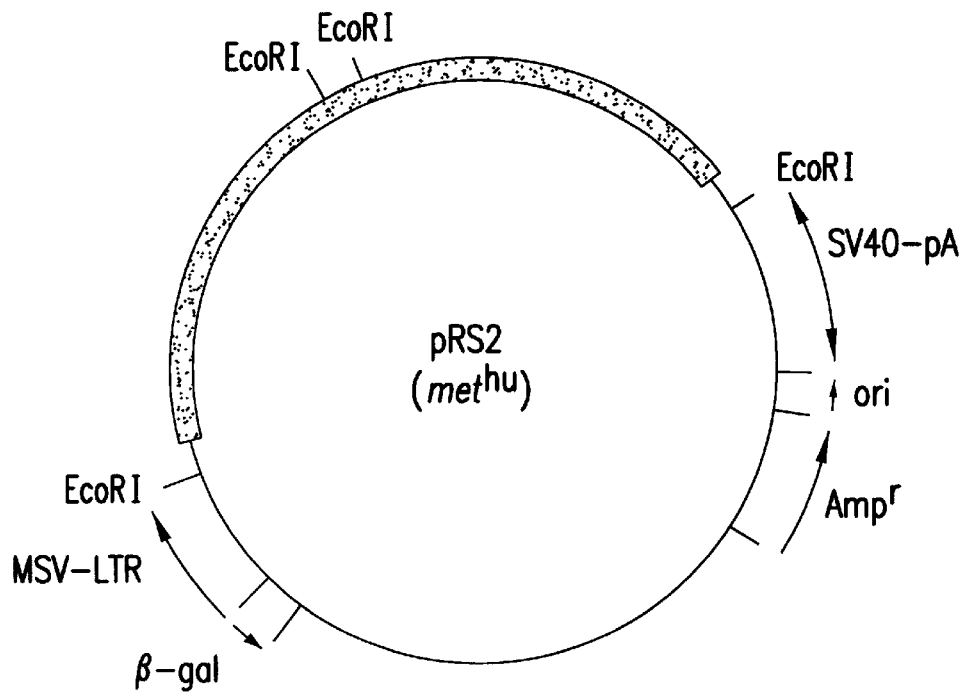
Figure 9B:
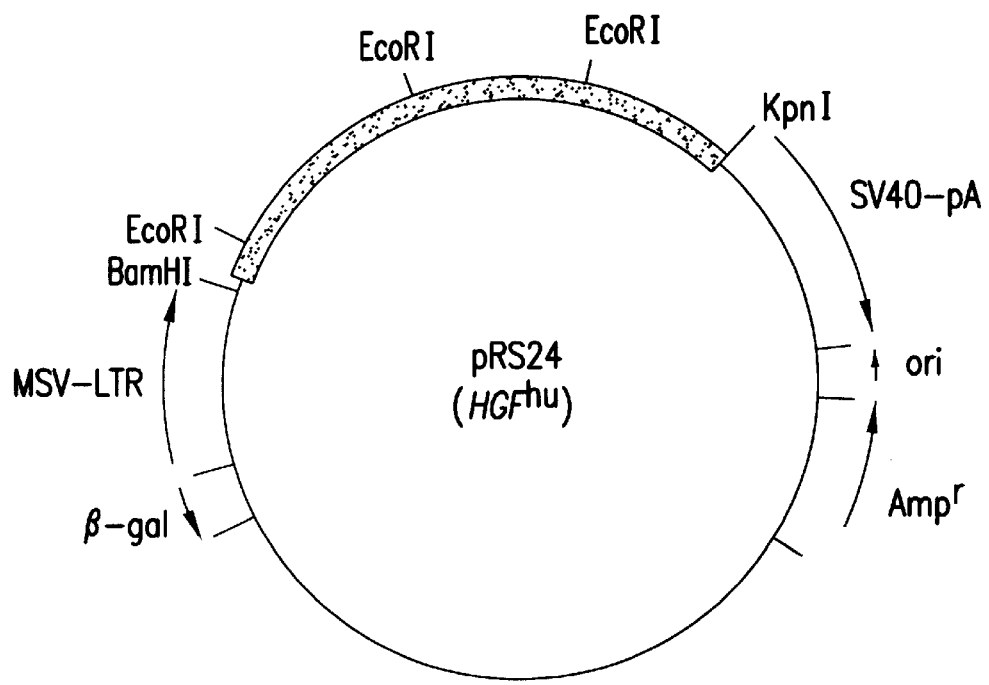

FIG. 9 is a diagram depicting the construction of plasmids pRS2 and pRS24 which are co-transfected into NIH/3T3 cells in the production of HGF/SF, as described in Example 2.

Figure 10A:
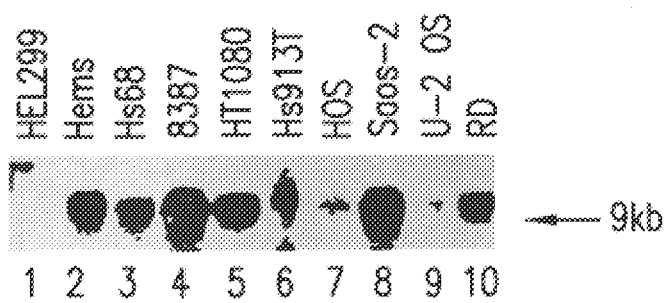
Figure 10B:
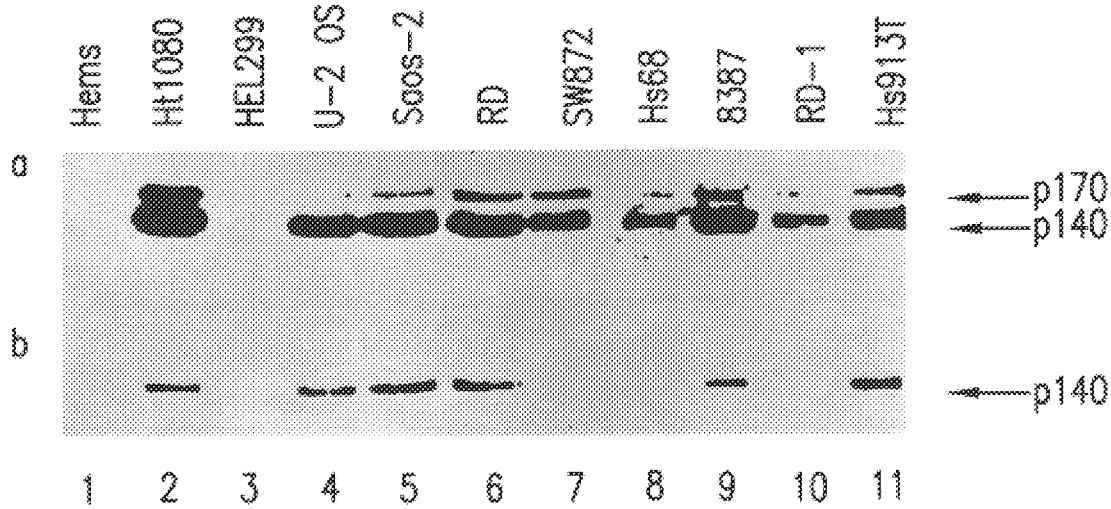
Figure 10C:
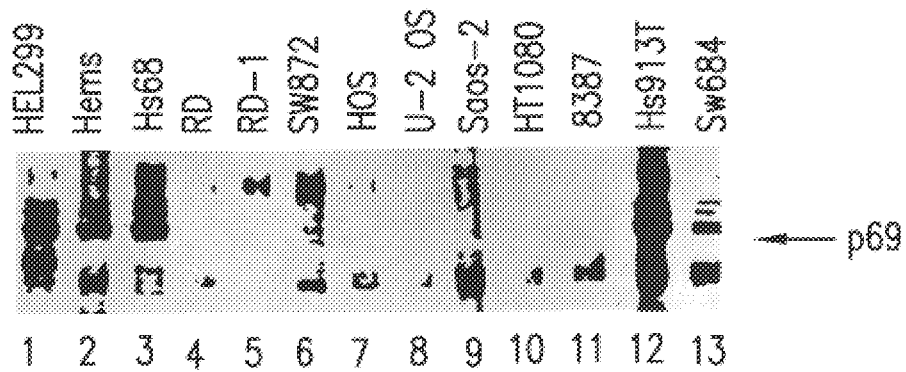

FIGS. 10A–C, illustrates Met and HGF/SF expression in human cells.

Panel A. Twenty μg of total RNA were loaded per lane for Northern analysis and full-length met$^{hu}$ cDNA was used as probe. Lane 1, HEL299; lane 2, Hems; lane 3, Hs68; lane 4, 8387; lane 5, HT1080; lane 6, Hs913T; lane 7, HOS; lane 8, Saos-2; lane 9, U-2 OS; lane 10, RD.

Panel B. One mg of cell lysate was immunoprecipitated with anti-C28 peptide antibody, followed by SDS-PAGE and immunoblotting with a Met monoclonal 19S antibody (a) or anti-P-Tyr antibody (b). Lane 1, Hems; lane 2, HT1080; lane 3, HEL299; lane 4, U-2 OS; lane 5, Saos-2; lane 6, RD; lane 7, SW872; lane 8, Hs68; lane 9, 8387; lane 10, RD-1; lane 11, Hs913T.

Panel C. Cells were metabolically labeled with [$^{35}$S] methionine and [$^{35}$S] cysteine (Translabel, ICN) for 6 h. One ml of supernatant was concentrated ten fold in a Centricon apparatus (Amicon; 10K cut-off); the volumes were adjusted to 0.35 ml with RIPA buffer for immunoprecipitation with HGF monoclonal antibody A3.1.2. Lane 1, HEL299; lane 2, Hems; lane 3, Hs68; lane 4, RD; lane 5, RD-1; lane 6, SW872; lane 7, HOS; lane 8, U-2 OS; lane 9, Saos-2; lane 10, HT1080; lane 11, 8387; lane 12, Hs913T; lane 13, SW684.

Figure 11:
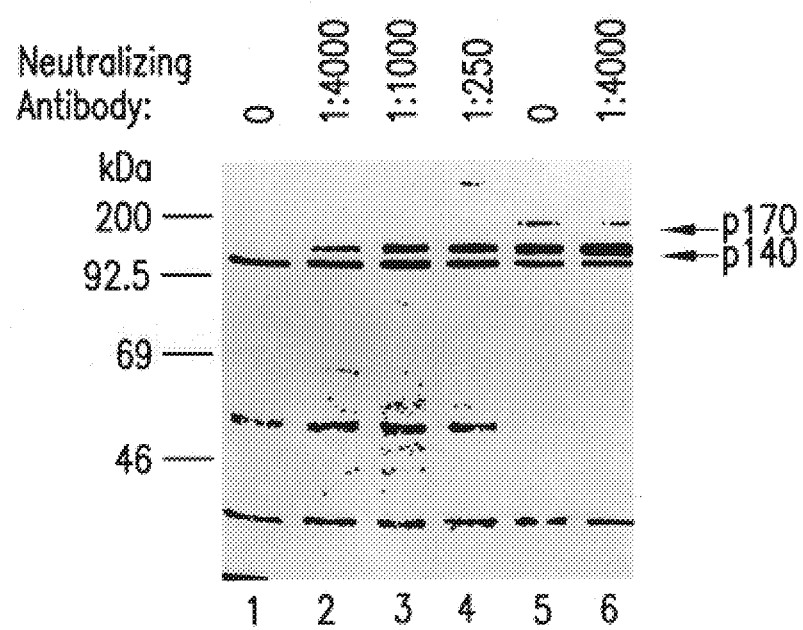
Figure 12A:
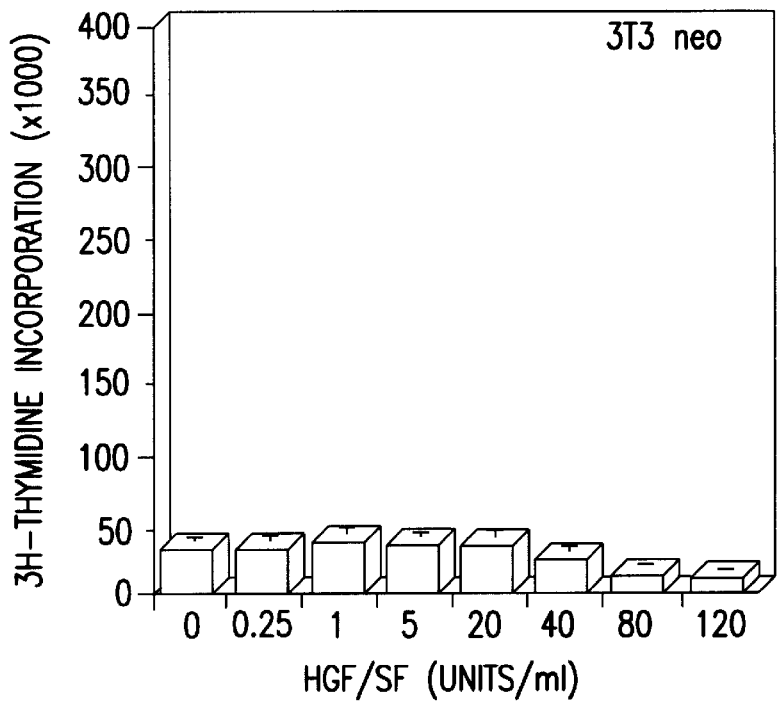
Figure 12B:
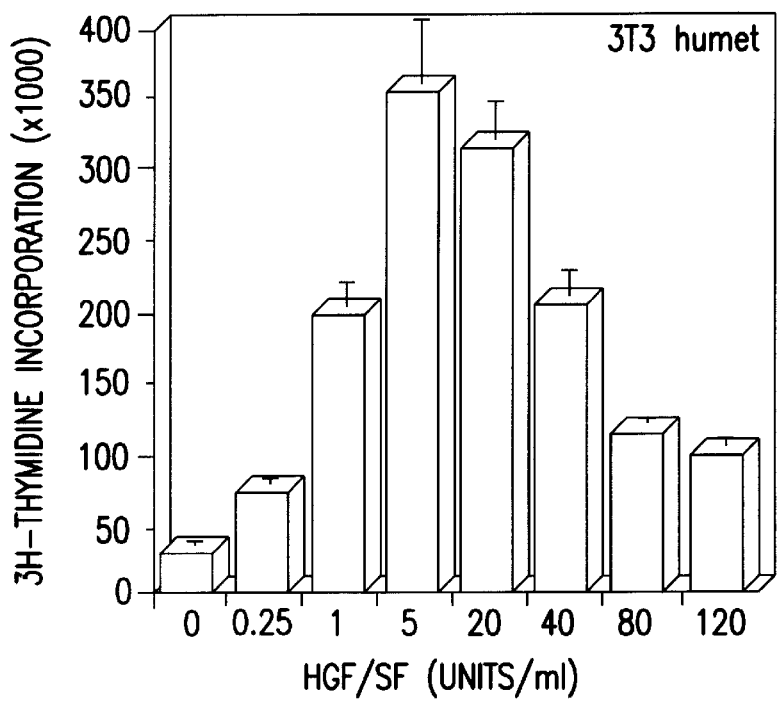
Figure 12C:
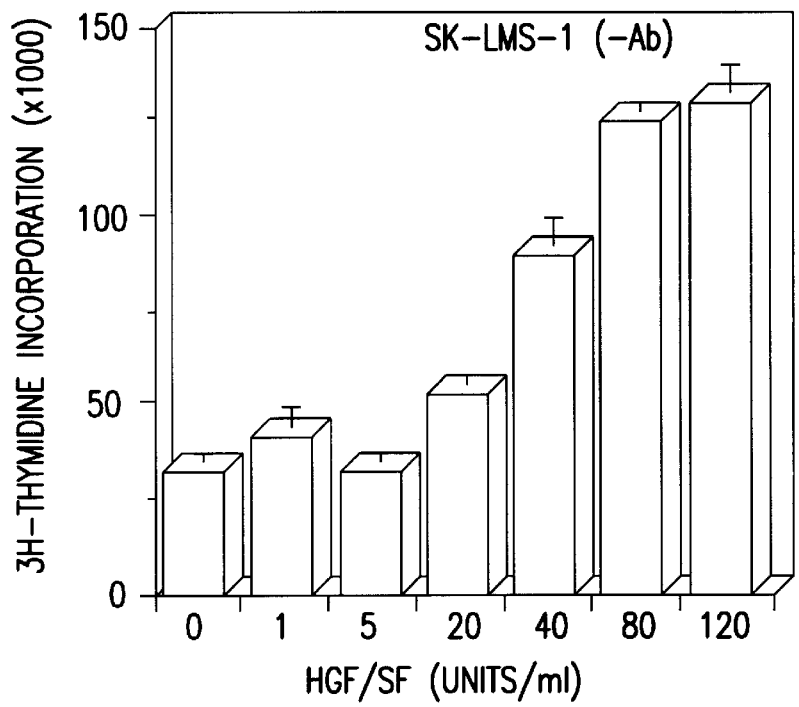
Figure 12D:
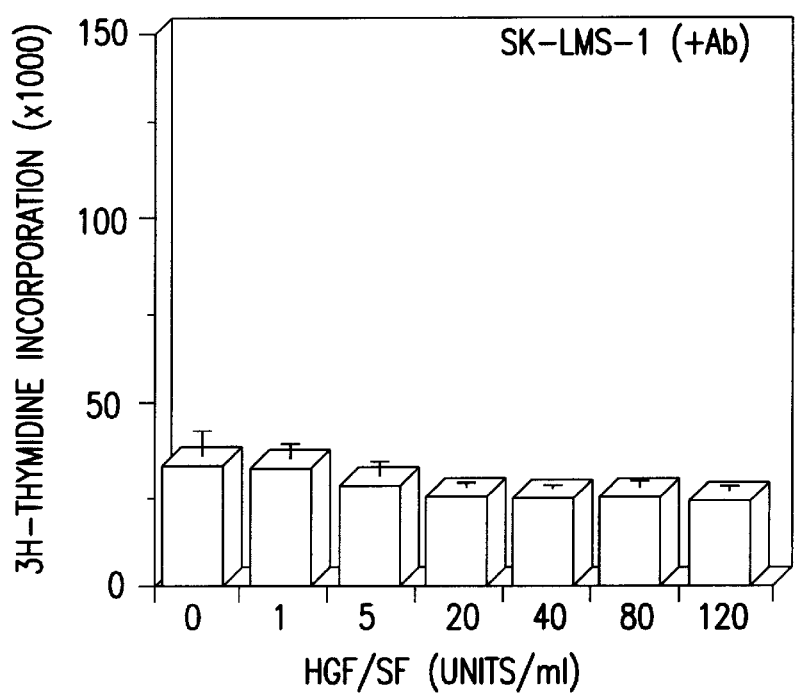

FIG. 11 shows that HGF neutralizing antibody increases Met protein abundance. Primary fibroblast HEL 299 (lanes 1–4) and Hems (lanes 5–6) cells were incubated for 48 hrs with or without HGF neutralizing antibody (anti-rhHGF-1): No antibody (lanes 1 and 5); 1:4000 (lanes 2 and 6), 1:1000 (lane 3), and 1:250 (lane 4) dilutions (antibody was added at zero time and at 24 h). Cells were lysed in RIPA buffer and 100 μg of protein were resolved by 7.5% SDS-PAGE and immunoblotted with 19S anti-Met$^{hu}$ monoclonal antibody.

FIGS. 12A–D, illustrates the mitogenic responses of NIH/3T3 fibroblasts and SK-LMS-1 human sarcoma cell line to HGF/SF stimulation.

Panels A and B. NIH/3T3 cells transfected with neo$^r$ or with neo$^r$ plus met$^{hu}$ cDNA (Rong et al., *Mol. Cell Biol.* 12: 5152 (1992)) were seeded into 96-well microtiter plates (Costar). After two days of serum starvation, the indicated concentrations of HGF/SF$^{hu}$ were added. After 4 h with $^3$H-thymidine, the cells were lysed and aliquots measured by scintillation counting. Each sample was done in triplicate. Normalized values of $^3$H-thymidine incorporation are shown.

Panels C and D. SK-LMS-1 human sarcoma cells were seeded and serum-starved as described for panels A and B. The indicated concentrations of HGF/SF were added in the presence or absence of HGF neutralizing antibody (anti-rhHGF-2) and incubated overnight. $^3$H-thymidine labeling was performed as described for panels A and B.

FIGS. 13A–D, illustrates the confocal analysis of human sarcoma tissues. Paraffin-embedded human tumor sections of leiomyosarcoma (Part A); chondrosarcoma (Part B); two different osteosarcomas (Parts C and D). Each paraffin section was double-stained with anti-Met C28 peptide antibody (FITC) and monoclonal anti-HGF/SF antibody 23C2 (Rhodamine). The immunofluorescence was determined by CLSM and color is generated by CLSM look up tables. High intensity is indicated by yellow, red is lower, and black is background. Met staining is green, HGF/SF is red, and yellow staining corresponds to cells that are stained and express both Met and HGF/SF. Magnification ×1000. In each figure, the insets are: (1) Nomarski; (2) Met staining and (3) HGF/SF staining. In the insets (2 and 3), yellow-red is used to characterize Met and HGF, respectively.

FIGS. 14A–F, shows the results of the in vitro invasive assay. Migration into a Nucleopore filter (8 $\mu$m pore size, Neuroprobe) through a reconstituted basement membrane Matrigel (Collaborative Research) was measured in 10 well Chemotaxis chambers (Neuroprobe). DMEM medium (Parts A, C–F) or DMEM with 200 U/ml HGF/SF$^{hu}$ (Part B) was placed in the lower well, and 10$^5$ cells (in DMEM with 1 $\mu$g/$\mu$l BSA) were placed in the upper well. The chamber was incubated at 37.5° C. for 24 hours. The Nucleopore filter was removed and non-invading cells on the upper surface were removed with a cotton swab after fixing in 70% Methanol and staining with Giemsa (Sigma). Cells remaining are invading cells. Parts A and B, MT cells; Part C, Tpr-Met cells; Part D, parental Met mu cells; Part E, parental HMH cells; Part F, HMH primary tumor explant cells.

Figure 15:
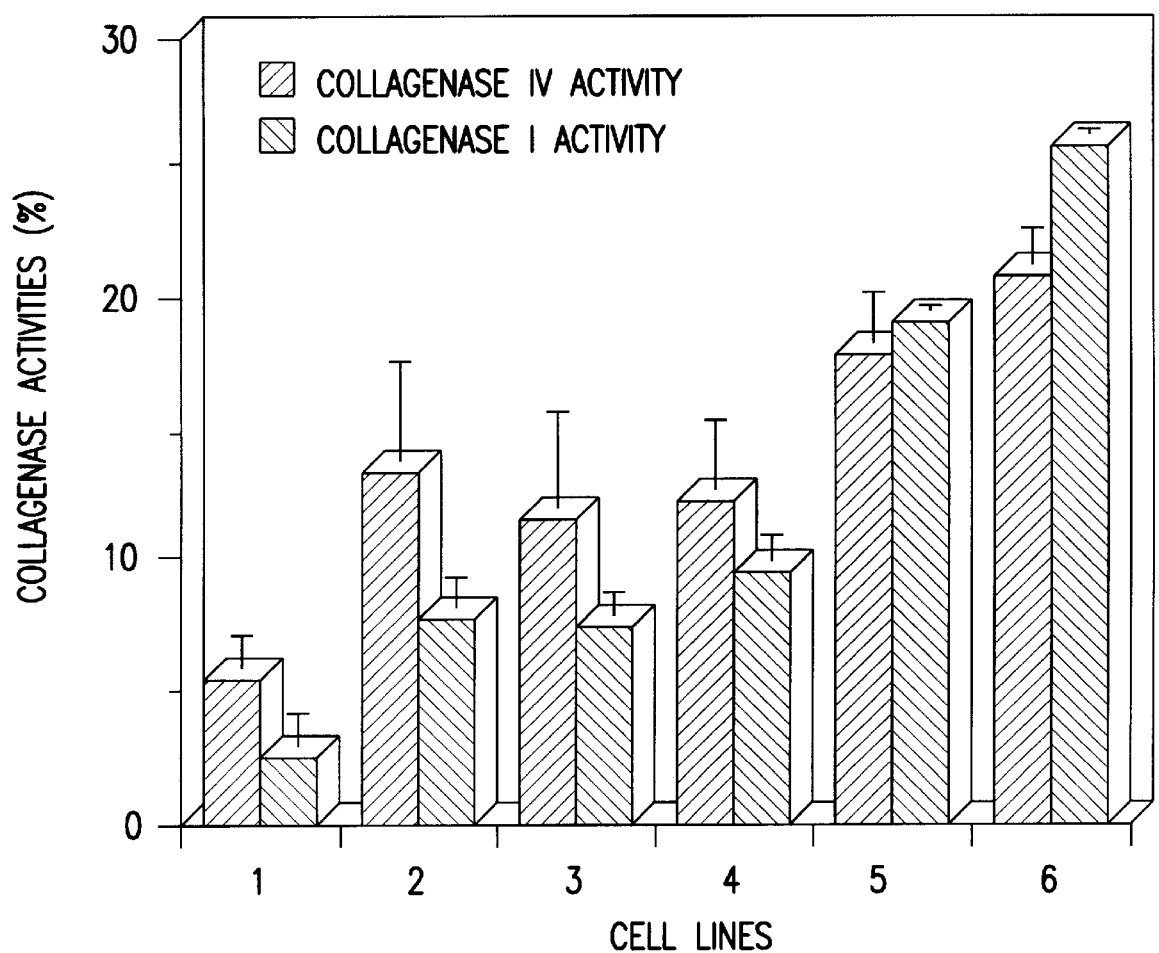

FIG. 15 shows the Type 1 and Type IV collagenase activity secreted by NIH/3T3 transfected cells. $^3$H-proline-labeled type I or type IV collagen (NEN) diluted with cold rat tail type I or type IV collagen (Sigma) (8000 cpm/6 $\mu$g in 0.5M acetic acid) was dried in 96-well plates. 2×10$^4$ cells were added, and after overnight incubation, supernatants from each well were precipitated with 10% TCA for radioactivity determinations. Collagenase activity was calculated as the percentage of bacterial collagenase activity which serves as a positive control. 1, NIH/3T3 cells; 2, Met$^{mu}$ cells; 3, Tpr-Met cells; 4, parental HMH cells; 5, primary HMH tumor explant cells; 6, secondary HMH tumor explants. Collagenase activity is an average of two experiments.

Figure 16A:
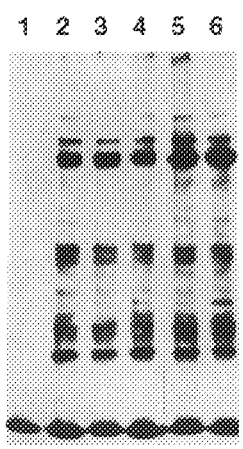
Figure 16B:
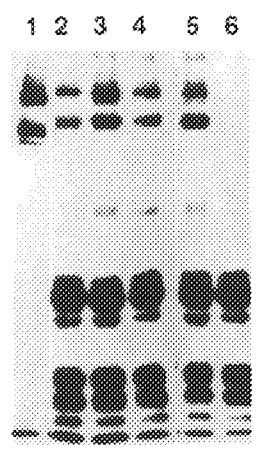
Figure 16C:
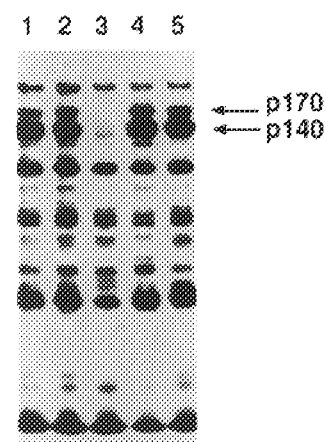

FIGS. 16A–C, shows the expression of Met and HGF/SF in lung metastases. Cell cultures were metabolically labeled with $^{35}$S methionine and $^{35}$S cysteine (ICN) for 6 hours. Cell lysates were immunoprecipitated with C28 anti-peptide antibody for Met$^{hu}$ (Part A) or SP260 anti-peptide antibody for Met$^{mu}$ (Part C). One half ml aliquots of medium were concentrated three-fold in a Centricon apparatus (Amicon, 10K cut off); the volumes were adjusted to 0.3 ml with RIPA buffer lacking reducing agent to allow efficient immunoprecipitation of p69α and p34B subunits and the p87 HGF/SF precursor with anti-HGF monoclonal antibody A3.1.2 (Part B). Part A and B, lane 1, NIH/3T3 cells; lane 2, secondary HMH tumor cells; lanes 3–6, HMH explanted lung metastasis from a primary tumor explant. Part C, lanes 1–2, explanted lung metastasis from Met$^{mu}$ cells; lane 3, NIH/3T3 cells, lanes 4–5, explanted lung metastases cells from Neo$^r$ control cells.

FIGS. 17A–F, presents photomicrographs that show the histopathology of metastatic tumors. Five $\mu$m sections of tissues from the subcutaneous metastasis assay were fixed in formalin and embedded in paraffin, mounted on superfrost slides, stained with hematoxylin and eosine (H&E) and evaluated by light microscopy. Part A, C and E, tumors from injection of 10$^5$ HMH 1° tumor cell explants; Parts B, D and F, tumors from injection of 10$^5$ Met$^{mu}$ 1° cell explants. Parts A and B, lung with multifocal metastatic tumors (T). Part C, heart with metastatic tumor (T) invading heart base and myocardium. Part D, submandibular salivary gland has been completely replaced by tumor cells (T). The parotid gland is in upper left corner and submandibular lymph node is in lower left corner. Epithelioid areas are evident in the large tumor mass. Part E, diaphragm with metastatic tumor (T) on pleural surface and invading muscle. Part F, retroperitoneal tumor (T) extending through muscle and fascial planes, and along a vertebral body (upper right).

FIGS. 18A & B, part A shows a comparison of HGF/SF production in parental NIH/3T3 cells transfected with Met and HGF/SF cDNAs (lanes 1 and 3) with production in tumor explant cells (lanes 2, 4 and 5) after tumorigenesis. The three isotopically-labeled protein bands represent p87 (HGF/SF uncleaved), p69α and p34β (cleaved subunits). By dramatic contrast, no amplification of HGF/SF occurs in tumor explants when the ligand is present in NIH/3T3 cells without Met (compare lane 7 with lanes 8–11).

Part B shows the testing of expression of HGF/SF using a method of reprecipitation that eliminates background and improves detection. See Rong et al., *Cell Growth Diff.*, 4: 563 (1993). These analyses show that the tumor explant cells from Met: HGF/SF tumors produce high levels of HGF/SF (lanes 1 and 2), while the tumors produced by HGF/SF cDNA do not (lanes 4 and 5). Thus, only the tumors produced with Met and HGF/SF produce high levels of the factor. See Rong et al., *Mol. Cell Biol.*, 12: 5152 (1992).

Figure 19A:
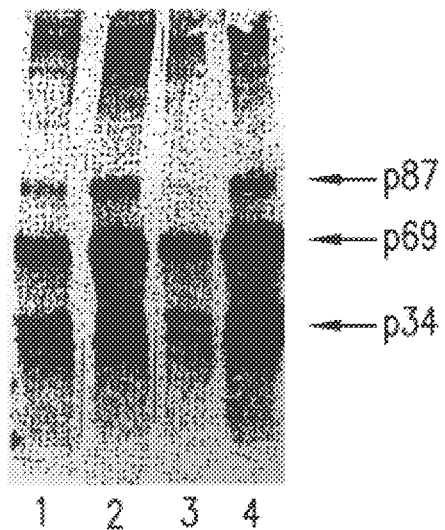

FIGS. 19A & B, part A is a radiograph of immunoprecipitates separated by SDS-PAGE that shows in lanes 1, 2, 3 and 4 that when C127 Met$^{mu}$ cells are super-transfected with LTR-HGF/SF$^{hu}$ cDNA, they express high levels of HGF/SF.

Part B is a radiograph of immunoprecipitates separated by SDS-PAGE that should HGF/SF$^{hu}$ expression in SK-LMS-1 human leiomyosarcoma cells. In lane 1, a pool of cells were transfected with neo$^r$ gene only; in lane 2, a pool of cells was transfected with HGF/SF$^{hu}$; in lanes 3 and 4, clones of cells were transfected with HGF/SF$^{hu}$. High levels of HGF are also expressed in these cells.

Figure 20:
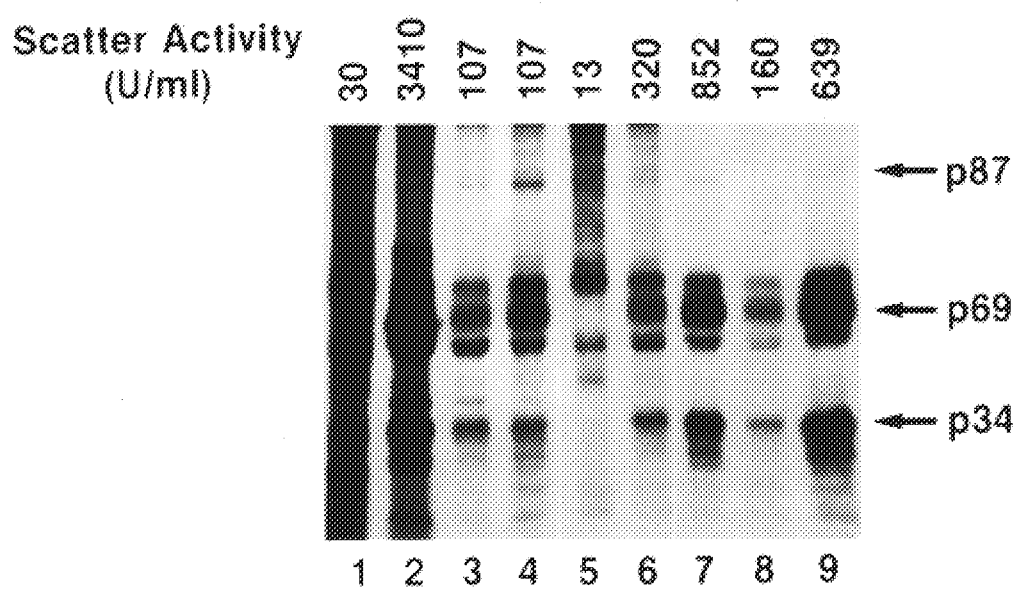

FIG. 20 shows scatter activity which directly parallels the level of HGF/SF protein in immunoprecipitates from labeled growth medium. Specifically, cells were metabolically labeled for five hours. The supernatant was concentrated and immunoprecipitated with human HGF monoclonal antibody A3.1.2. Lane 1, shows SK-LMS-1 transfected with neo$^r$. Lane 2 shows a pool of SK-LMS-1 cells with HGF/SF$^{hu}$. Lanes 3–5 show tumor explants of lane 2. Lane 6 shows a clone of SK-LSM-1 with HGF/SF$^{hu}$. Lanes 7–10 show tumor explants of lane 6.

FIG. 21 presents data related to Met and HGF/SF expression in human fibroblast and sarcoma cell lines.

FIG. 22 shows the results of an in vitro motility invasiveness assay.

FIG. 23 presents two tables showing Met-mediated experimental lung metastasis in athymic mice (A) and experimental metastasis in immune competent triple deficiency mice (B).

FIGS. 24A & B, presents two tables showing Met-mediated spontaneous metastasis in athymic mice which were injected subcutaneously (A) and injected in the mammary fat pad (B).

DETAILED DESCRIPTION OF THE PREFERRED EMBODIMENTS

In one embodiment, the present invention involves a method of preventing tumor cell metastasis comprising treating a tumor-bearing mammal with a medicament containing a tumor-metastasis inhibiting amount of a substance that prevents the binding of HGF/SF with Met. By the term "treating" is meant diminishing or arresting tumor metastasis in a tumor-bearing mammal.

In another embodiment, the invention relates to a method of preventing the further development of a mesenchymal tumor comprising administering to a mesenchymal tumor-bearing mammal a medicament containing a tumorigenesis-inhibitory amount of a substance that prevents HGF/SF from binding with Met.

In these embodiments, the preferred mammal is a human. The term "medicament" is intended to mean a pharmaceutically acceptable composition comprising a metastasis-inhibiting or tumorigenesis-inhibitory amount of a substance that prevents the binding of HGF/SF with Met in admixture with suitable pharmaceutically acceptable vehicle and optionally other additives. Pharmaceutically acceptable compositions are those that permit the biological activity of the active ingredients to be unequivocally effective, and which contain no additional components which are toxic to the subject to which the compositions would be administered. Other additives include carriers and excipients well known to the skilled artisan. See *Remington's Pharmaceutical Sciences* (18th ed.) Mack Publishing, Easton Pa. (1990). A "tumor-metastasis inhibiting amount" or "tumorigenesis inhibitory amount" will vary depending upon the mammal to be treated, with consideration given to the age, weight and physical condition of the mammal, as well as to the size and type of tumor. The exact amount can be determined by the skilled practitioner using methods of formulation and testing that are routine and well within the skill of the art.

The term "tumorigenesis" means the production of new growth or growths. It is generally accepted in the art that for tumor cells to become "metastatic", a number of coordinated events must take place. For instance, metastasis involves the process whereby cancer cells penetrate the walls of the vascular and lymphatic circulatory systems, enter the circulatory system, lodge ("adhere") in a "downstream" capillary bed or lymph node and leave ("movement/mobility") the circulatory system to penetrate into normal stromal tissue. For these processes to occur, the tumor cell must acquire invasive properties. Invasive properties include (1) the ability of cells to adhere to the extracellular matrix (due to receptors on cell surface—such as the integrins); (2) the induction of destruction enzymes ("metalloproteases") which break through the extracellular matrix—such as collagenases and plasminogenases; and (3) the migration of cells through the "holes" created by enzymatic destruction. Increases in the levels of metalloproteases secreted by cells, increases in motogenicity of cells, and changes in the pattern of expression of receptors, involved in attachment (integrins) have all been noted, and in some cases, correlate with the metastatic potential of human carcinoma cells. (L. A. Liotta, *Scientific American,* 54–63 (Feb. 1992)).

It is known that HGF/SF increases the levels of activity of at least two of these events: the secretion of collagenases and plasminogenases and motogenicity. Furthermore, HGF/SF is known to be angiogenic and angiogenesis is important for the survival of tumor cells. (J. Behrens et al., *J. Cell Biol.* 108: 2435–2447 (1989); K. M. Weidner et al., *J. Cell Biol.* 111: 2097–2108 (1990)). By the term "motogenesis" is meant the process whereby continuous sheets of cells disaggregate, change morphology and become motile. (E. Gherardi and M. Stoker, *Cancer Cells* 3: 227–232 (1991)). This phenomenon is also referred to as "scattering."

Applicants stress that "mitogenesis" and "motogenesis" (or "scattering") are two different events. While both tumorigenic and metastatic cells are highly mitogenic, metastatic cells additionally exhibit increased attachment to host cellular or extracellular matrix, enhanced proteolysis of host basement membrane, increased cell motility and the ability to colonize target organs. (Liotta, *Scientific American* 266: 54 (1992)). Several oncogenes including src, ras (Chambers et al., *Mol. Cell Biol.* 5: 728 (1985); Egan et al., *Mol. Cell Biol.* 7: 830 (1987); Hill et al., *Nat'l. Can. Inst.* 80: 484 (1988); Creig et al., *Proc. Nat'l. Acad. Sci. U.S.A.* 2: 3698 (1985); Thorgeirsson et al., *Mol. Cell Biol.* 5: 259 (1985); Bradley et al., *Proc. Nat'l. Acad. Sci. U.S.A.* 83: 5277 (1986)), and neu (Yu et al., *Oncogene* 6: 1991 (1991)), confer increased tumorigenic and metastatic properties to NIH/3T3 cells in nude mice.

Applicants have demonstrated that HGF/SF induces motogenicity in two ways. See Example 1, below. First, as shown in Table 1, cells which display a classical scattering response to HGF/SF showed rapid phosphorylation of endogenous met receptor on tyrosine, suggesting that scattering is activated through the met receptor.

TABLE 1

| Cell Line | Mitogenicity Index | Scattering (w/HGF) |
|---|---|---|
| Bix2NMA | 1 | +++ |
| Calu-1 | 1 | ± |
| SW620 | 1.7 | ++ |
| HT29 | 1 | + |
| HCT116 | 1.5 | + |

[1]Mitogenicity index = $^3$H-thymidine incorporation in presence of HGF/$^3$H-thymidine incorporation without HGF.

Paracrine Met-HGF/SF signal transduction produces mitogenic, motogenic, and morphogenic responses in a cell type dependent fashion, properties that contribute to tumor invasion and metastasis. Example 7 shows that Met$^{mu}$ and HMH cells are invasive in vitro in Boyden chamber basement membrane matrigel assays. These cells secrete type I and IV collagenase, showing that autocrine Met-HGF/SF signal transduction enhances fibroblast cell motility and induces the protease activity necessary for matrigel invasion. In experimental and spontaneous metastasis assays, Met$^{mu}$ or HMH cells metastasize to the lung. However, lower numbers of subcutaneously injected Met$^{mu}$ and HMH cells produced invasive tumors in the diaphragm, salivary gland, and retroperitoneum. With tumor passage in nude mice, Met expression increases (Rong et al., *Cell Growth & Diff.* 4: 563 (1993)), enhancing the activity of Met$^{mu}$ and HMH cells in in vitro and in vivo metastasis assays. Autocrine mediated Met-HGF/SF signal transduction in NIH/3T3 mesenchymal cells may be an important system for understanding the biological process of metastasis.

Applicants also have performed vigorous testing on mouse breast tumor "epithelial" cell line (C127 cells) transfected with mouse and human met cDNA's encoding the met proto-oncogene product, to show scattering in response to HGF/SF only in cells that express the met product from exogenously introduced met cDNA, but not in the non-transfected cells. These results are shown in Table 2:

TABLE 2

| Cell Line | Mitogenicity Index | Scattering (w/HGF) |
|---|---|---|
| C127 | –[a] | — |
| C127 – met$^{hu}$ | ++ | ++ |
| C127 – met$^{mu}$ | +++ | + |

[a]Stimulation of $^3$H-thymidine incorporation is presumed to be due to low levels of exogenous c-met product in C127 cells.

Inactivation of the HGF/SF-Met pathway provides the basis for the therapeutic methodologies of the present invention, designed to prevent tumor cell metastasis. These methodologies include the production of medicaments containing substances which prevent the binding of HGF/SF with Met. Such substances include, but are not limited to, HGF/SF or Met variants, HGF/SF or Met mimetics, and antibodies or antibody fragments against HGF/SF or Met which prevent HGF/SF binding with Met.

"Variants" include, for example, oligopeptides and polypeptides which are HGF/SF species that lack or possess impaired met-binding domain, or that lack or possess an impaired activating domain, but that otherwise retain the structural and biochemical characteristics of HGF/SF. Similarly, variants include Met species that lack or possess an impaired HGF/SF-binding domain, or lack or possess an impaired tyrosine kinase domain, but which otherwise retain the structural and biochemical characteristics of the met protein. See, e.g., Lokker et al., *EMBO J.* 11(7): 2503 (1992).

HGF/SF and Met species which qualify as variants according to the present invention can be produced pursuant to the present invention by conventional genetic engineering techniques. For example, variants can be produced by techniques which involve site-directed mutagenesis. See "Mutagenesis of Cloned DNA," in *Current Protocols in Molecular Biology*, 8.0.3 et seq. (Ausubel, et al. eds. 1989); Lokker et al., supra.

Variants of the present invention also include, for instance, a soluble form of Met consisting of the extracellular HGF/SF-binding domain that acts as an antagonist of normal Met binding with HGF/SF. Such variants can be produced through molecular modelling techniques well known in the art of the invention. See, e.g., Fuh et al., *Science* 256: 1677–1680 (1992).

A metastasis-inhibiting variant of the present invention also can be a naturally occurring variant, such as HGF/NK2 or HGF/NK1, disclosed in U.S. co-pending application Ser. No. 08/130,134, which is hereby incorporated by reference. HG/NK2 is a truncated form of HGF/SF encoded by alternative HGF transcripts which specify a sequence that includes the N-terminal and first two kringle domains. HGF/NK1 is another truncated form of HGF/SF encoded by HGF/SF transcripts which specify the sequence that includes the N-terminal and only the first kringle domain.

The metastasis-inhibiting substance of the present invention may be an HGF/SF or Met "mimetic." One example of a mimetic is an anti-idiotype antibody, that is, an antibody which is produced by immunizing an animal with an antibody which specifically binds to an epitope on an antigen. The anti-idiotype antibody recognizes and conforms to the combining site on the first antibody. Therefore, the shape of its combining site closely resembles the epitope which fits into the combining site of the first antibody. Because an anti-idiotype antibody has a combining site which mimics the original antigen, it can be used as a ligand for binding with the receptor to the original antigen. See Fineberg & Ertl, *CRC Critical Reviews in Immunology* 7: 269–284 (1987). Appropriate mimetics of HGF/SF could be identified by screening with an HGF/SF antibody to detect which compounds bind thereto or could be produced by molecular modelling. See Morgan et al., "Approaches to the Discovery of the Non-Peptide Ligands for Peptide Receptors and Peptidases," in *Annual Reports in Medicinal Chemistry* (Academic Press 1989), at pages 243 et seq.

The metastasis-inhibiting substance of the present invention also can be an antibody or antibody fragment against HGF/SF or Met which inhibits binding of HGF/SF with Met. An "antibody" in accordance with the present invention includes a whole antibody and parts thereof, either alone or conjugated with other moieties. Antibodies include polyclonal antibodies, monoclonal antibodies, and single chain antibodies. Antibody fragments are those that bind HGF/SF or Met, including Fab and F(ab)$_2$ fragments, inter alia. The antibodies of the present invention can be made in animals or by recombinant DNA techniques well-known to the skilled artisan.

Figure 6A:
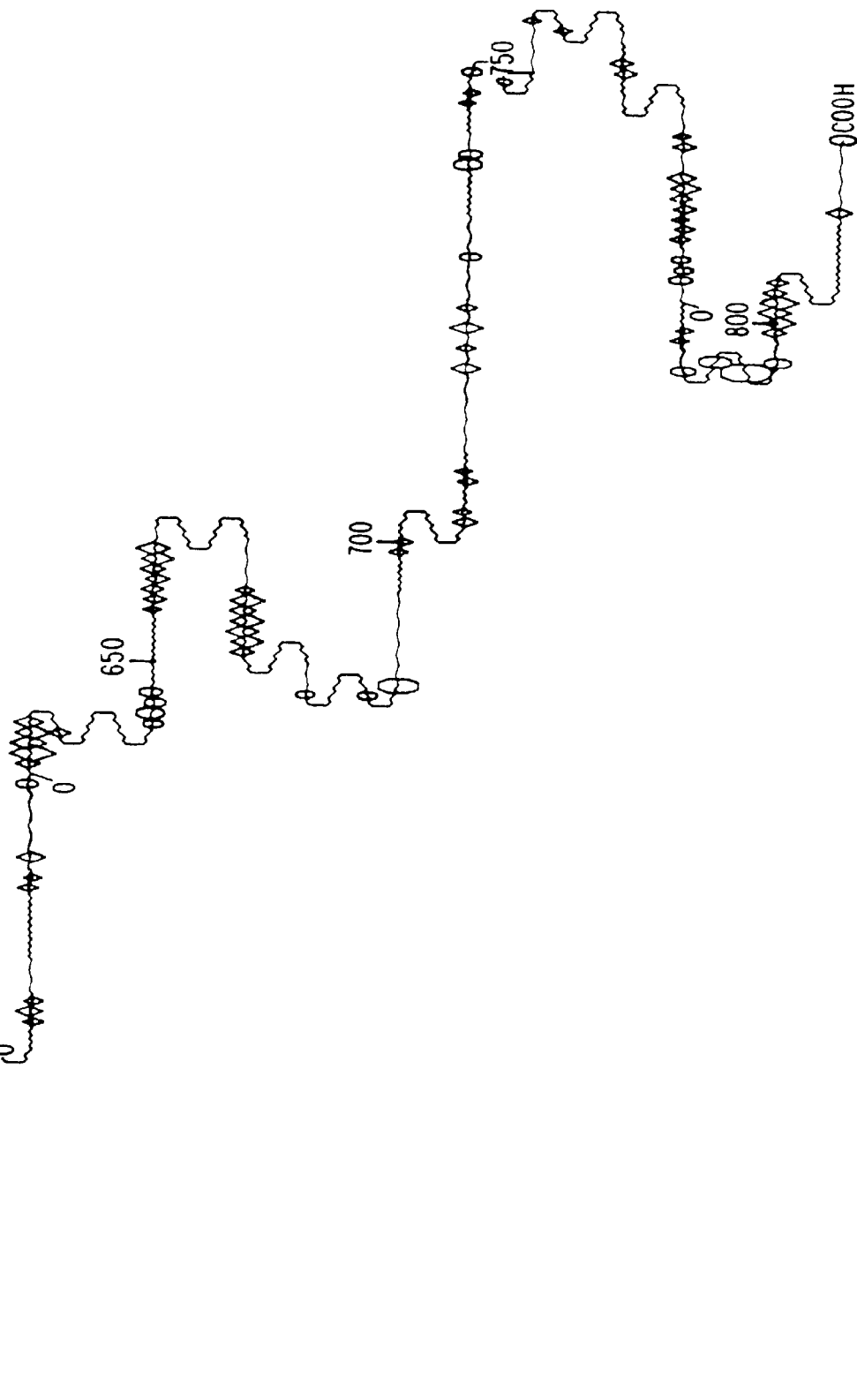
FIG. 6 shows a comparison of the computer-generated predicted structure of the amino acid sequence between the conserved NdeI-PvuII sites in the human Met (top) with mouse Met sequence (bottom). The amino acid sequence of human and mouse Met (between the Nde I-Pvu II sites) is depicted in the inset box—highlighted are regions where the amino acid sequence is less conserved (conservation is depicted by dashed lines between the human and mouse sequence). The less conserved domains within the Nde I-Pvu II segment of cDNA conferring transforming potential onto Met either reflect domains directly involved in ligand binding, or through structural characteristics modulate either ligand binding or activation of the receptor following ligand binding. Therefore, applicants generated polyclonal antibodies to synthetic peptides corresponding to these sequences. Antibodies to the first domain were generated in rabbits against human sequence (α 1240) and mouse sequence (α 1241); antibodies to the second domain were generated against human sequence (α 1242)(amino acids 780–805) and mouse sequence (α 1243). Only 1242 and 1243 precipitated human and murine c-met protein, respectively.
Figure 6C:
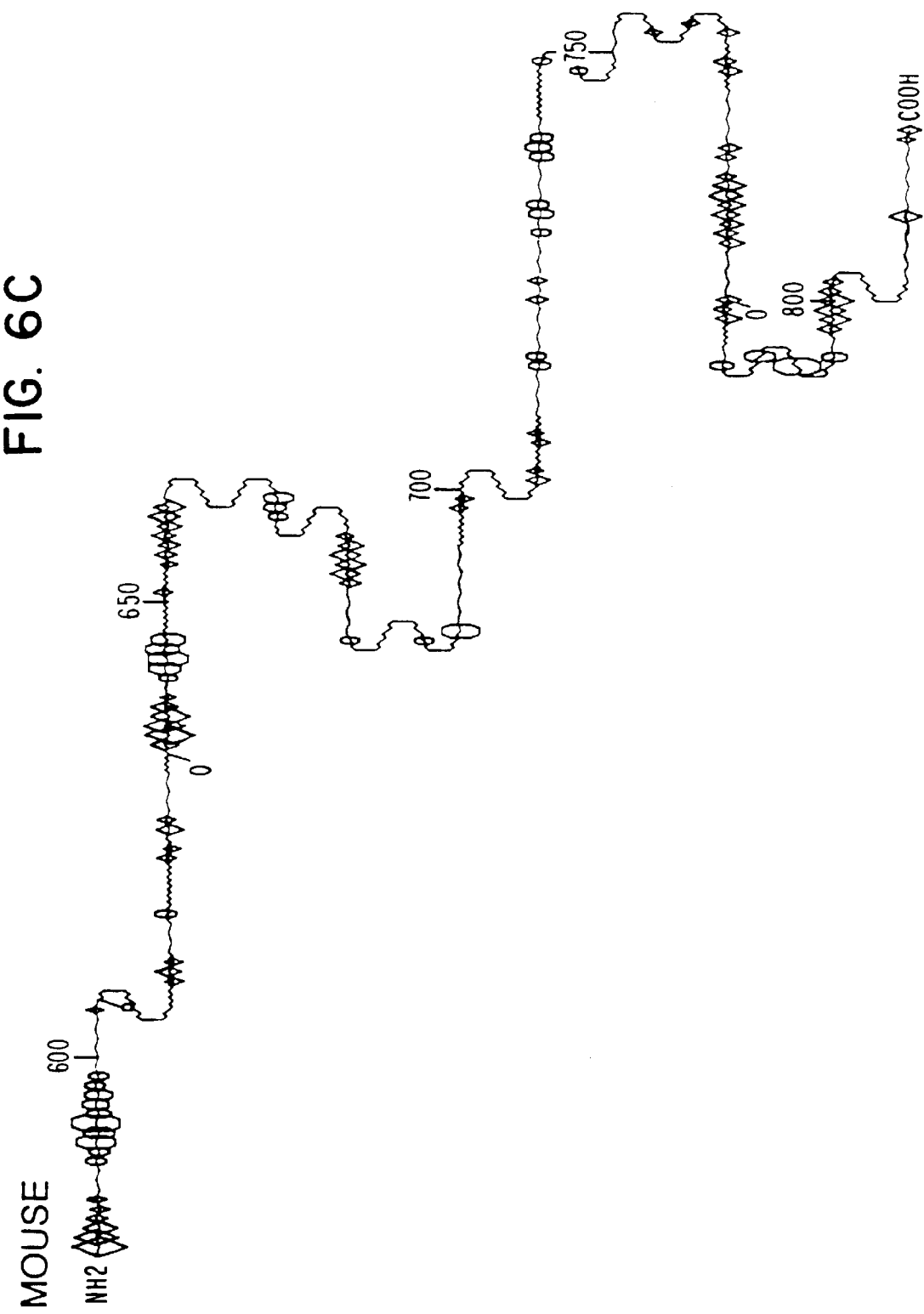

In one embodiment of the present invention, applicants produce polyclonal antibodies against synthetic peptides corresponding to Met extracellular domains involved in ligand binding or the modulation of ligand binding. See FIGS. 6 and 7 and description thereof.

Applicants have developed a protocol for the in vitro testing of inhibitors of ligand binding directed against Met which measures the ability to block tumor invasion or metastasis. For example, applicants have discovered that NIH/3T3 cells transfected with HGF/SF and met$^{hu}$ are "invasive" in a Boyden-chamber assay, as are cells with met$^{mu}$ (which produce murine HGF/SF endogenously) and the oncogenic form of met, tpr-met. Similarly, met$^{hu}$ transfectants are invasive when in "conditioned medium," i.e., medium containing HGF/SF$^{hu}$. Applicants have further discovered that "1242" polyclonal antibodies generated against a peptide sequence within the extra-cellular domain of Met, blocks the invasive potential of the tumor cells. This peptide is further described in FIG. 6, where it is the second highlighted domain, amino acids 780–805.

Indeed, chimeric mouse/human experiments, such as those disclosed in Example 2 and discussed with reference to FIG. 5, enable the definition of domains of the Met receptor and HGF/SF which are involved in ligand/receptor binding. Through mathematical, computer assisted computations, such as those shown and described under FIG. 6, it is possible to define regions within the domains which are different in the mouse and human. These "differences" may modulate species specificity in responses to HGF/SF and antibodies against such regions can be tested for their ability to inhibit HGF/SF binding. Thus, applicants have provided a method, applicable to the development of compositions for in vivo use, for in vitro testing of tumor metastasis inhibition.

In addition, applicants have provided an in vivo assay for the determination of effective dosages of Met binding inhibitors. Example 7 discloses a method for inducing lung metastases in athymic mice by subcutaneously injecting Balb/c nu/nu mice with NIH/3T3 cells that have been transfected with the oncogenic form of met (tpr-met cells), met$^{hu}$ (Met$^{hu}$ cells) or met$^{hu}$ and HGF/SF$^{hu}$ (HMH cells). Following this treatment, various dosages of Met binding inhibitors can be administered to optimize a treatment protocol. In this in vivo assay, the efficacy of a particular treatment regimen for inhibiting tumor metastasis is determined by histological examination of lung tissue.

The delivery of the tumor metastasis-inhibiting substance of the present invention to the selected site of action may be achieved using conventional methods of drug delivery, gene transfer, or any combination thereof. See K. J. Van Zee et al. *PNAS* 89: 4845–49 (1992). Means for delivery include conjugation to a carbohydrate or carrier protein; administration with any slow release complex recognized in the field; compounding in other delivery systems, such as microspheres or liposomes; or administering in an expression vector system. One method of delivery applicable to the present invention involves the coupling of the tumor metastasis-inhibiting substance of the present invention to polyethylene glycol or polypropylene glycol to produce a physiologically active non-immunogenic water soluble composition, according to the method of Davis et al., U.S. Pat. No. 4,179,337.

Administration of such a composition may be accomplished by any method known to the skilled artisan. For instance, the composition may be in an aqueous solution which is injected into the mammalian circulatory or intramuscular system. As noted above, the determination of the proper dosage depends upon a number of case specific variables, including the age and weight of the mammal, and involves routine experimentation within the expertise of the skilled artisan.

In one embodiment, the invention relates to a method of preventing the metastasis of tumors of mesenchymal origin, such as sarcomas. The term sarcoma is intended to include, but is not limited to osteosarcoma, chondrosarcoma, fibrosarcoma, Ewings tumor, reticulum cell sarcoma, giant-cell tumor, leiomyosarcoma and other tumors set-forth in FIG. 21. In another embodiment, the invention relates to a method of preventing the further development of a mesenchymal tumor by administering to a mesenchymal tumor-bearing subject a tumorigenesis-inhibitory amount of a substance that prevents HGF/SF from binding with Met.

In another embodiment of the present invention, artificial activation of the HGF/SF-Met pathway provides the basis for therapeutic methodologies designed to restore, replace, or enhance naturally occurring biological activities. These methodologies include delivery to the site of activation HGF/SF or Met variants or mimetics which enhance the binding interaction between Met and HGF/SF and thereby create an artificially sustained HGF/SF-Met interaction that would prevent signal transduction. For example, site-directed mutagenesis of the HGF/SF-binding domain of Met, or the Met-binding domain of HGF/SF (or both) may be used to create a member of the HGF/SF-Met pair with higher binding affinity for the other member of the pair and thus affect accelerated growth or regeneration of wounded tissue. Similarly, conventional recombinant DNA techniques could be used to enhance or sustain the kinase activity of the Met protein normally regulated by HGF/SF binding, including Met mutations possessing a constitutively activated tyrosine kinase. Activation of the HGF/SF-Met pathway by means of supplementing the natural expression of Met by recombinant DNA techniques in combination with exogenously administered HGF/SF is also included within the scope of the invention.

Delivery of genetically engineered HGF/SF or Met species to the selected site of action can be achieved using conventional methods of drug delivery, gene transfer, or any combination thereof, as discussed above in connection with the delivery of substances which inhibit tumor metastasis.

In another embodiment of the present invention, applicants present a method for producing human HGF/SF. Specifically, applicants have discovered that eukaryotic cells express surprisingly high levels of HGF/SF from a transfected long terminal repeat (LTR) vector recombinant construct containing human HGF cDNA. Applicants have discovered that the highest levels of HGF are detected in eukaryotic cells when an LTR human c-met proto-oncogene (cDNA vector) is co-transfected with the human LTR/HGF construct and cells are derived from secondary tumors. Preferably, these eukaryotic cells are mammalian cells. For example, applicants show in Example 2, the production of HGF/SF in NIH/3T3 cells. In Example 9, applicants show the expression of HGF/SF in mouse C127 cells and in human leiomyosarcoma cells. However, one advantage of the NIH/3T3 cell line, in particular, is that the transformed cells can grow to high cell density. Accordingly, this cell line produces extremely high levels of HGF/SF, about 1 mg of HGF/SF per liter (1250 units per ml). Applicants also have shown in Example 10 and 11 that C127 and SK-LMS-1 cells, respectively, similarly over express HGF/SF, when transfected in accordance with the present invention. Applicants note that in comparison, another cell line which endogenously produces HGF/SF, and which is derived from human keratinocytes, ndk cells, produces approximately 10 $\mu$g per liter per 48 hours. See J. C. Adams, et al., *Science* 98: 385–394 (1991); E. M. Rosen, et al., *BBRC* 168(3): 1082–1088 (1990). It is therefore unexpected to obtain the yield of 1 mg/liter of HGF/SF from NIH/3T3 cells and to observe similar overexpression of HGF/SF in other mammalian cells co-transfected with the recombinant vector constructs of the present invention.

Although applicants have demonstrated high levels of HGF/SF expression in mouse and human cells expressing Met, those of skill in the art would recognize that other eukaryotic cells could be used in the present invention. Eukaryotic cells include mammalian and insect cells.

Examples of mammalian cells include Chinese hamster ovary cells (CHO-KI; ATCC CCL61); rat pituitary cells (GH1; ATCC CCL82); HeLa S3 cells (H-4-II-E; ATCC CRL 1548); SV40 transformed monkey kidney cells (COS-1; ATCC CRL 1650): murine embryonic cells (NIH/3T3; ATCC CRL 1658); C127 mouse cells (ATCC 1616) and human tumor cells (SK-LSMS-1; ATCC HTB88). Non-mammalian eukaryotic cells include insect cells, such as *Spodoptera frugiperda* cells Sf-21 and Sf-9 (Vaughn, L. et al., *In vitro* 13, 213–217 (1977)).

Thus, one embodiment of the present invention relates to a method of producing HGF/SF comprising the steps of:

(a) transfecting eukaryotic cells with DNA encoding HGF/SF$^{hu}$ and Met$^{hu}$;

(b) introducing cells transfected in accordance with step (a) into a mammal, thereby generating a primary tumor;

(c) explanting and propagating cells of the primary tumor in vitro;

(d) selecting those cells propagated in accordance with step (c) which express high levels of HGF/SF$^{hu}$ and high levels of Met$^{hu}$;

(e) introducing cells selected in accordance with step (d) into a mammal thereby producing a secondary tumor;

(f) explanting and propagating cells of the secondary tumor in vitro; and (g) obtaining HGF/SF$^{hu}$ produced by the cells of step (f). The cells are grown in serum and protein free medium.

Thus, the DNA of the present invention comprises a first DNA vector comprising, in operable linkage, a promoter derived from a long terminal repeat of a retrovirus, DNA encoding the entire coding domain of a receptor protein and a polyadenylation signal and a second DNA vector comprising, in operable linkage, a promoter derived from a long terminal repeat of a retrovirus, DNA encoding a ligand for said receptor of said first DNA vector and a polyadenylation signal.

In the preferred embodiment, the DNA of the present invention comprises a first DNA vector comprising, in operable linkage, a promoter derived from a long terminal repeat of a retrovirus, DNA encoding the entire coding domain of human Met and a polyadenylation signal and a second DNA vector comprising, in operable linkage, a promoter derived from a long terminal repeat of a retrovirus, DNA encoding human HGF/SF and a polyadenylation signal.

Although the production of the DNA vectors of the present invention may be accomplished by a variety of methods known to the skilled artisan, production is exemplified in Example 2, in the discussion of cDNA plasmid constructs and cell lines. The preferred DNA vectors of the present invention are depicted in FIG. 9.

Cells transfected with HGF/SF$^{hu}$ and Met$^{hu}$ LTR-cDNA are introduced into mammals, according to methods well-known in the art, preferably by injection. See Blair, D. G., et al., *Science* 218: 1122–1125 (1982). The preferred mammals of the present invention are nude mice. Primary tumors which develop in these mammals after 5–10 weeks are explanted and propagated in in vitro culture, as described in Example 2, with regard to "nude mouse assays" In vitro propagated primary tumor cells are then subjected to immunoprecipitation analysis to ascertain which cells expressed high levels of HGF/SF$^{hu}$ and high levels of Met$^{hu}$. See FIG. 3 and the above description thereof. For instance, explanted cells may be metabolically labeled and then immunoprecipitated with Met$^{hu}$ monoclonal antibodies (monoclonal 19S), concentrated, then immunopreciptated with HGF/SF$^{hu}$ monoclonal antibody A3.1.2. High levels of HGF/SF$^{hu}$ and Met$^{hu}$ are determined with reference to expression levels in the starting material. Thus, any level of expression higher than that observed in the starting material is considered "high" for purposes of this method. Cells expressing high levels of HGF/SF$^{hu}$ and Met$^{hu}$ are then introduced into mammals and secondary tumors which develop are explanted and propagated in vitro, according to methods well-known in the art. See Blair, D. G., et al., *Science* 218: 1122–1125 (1982).

HGF/SF$^{hu}$ expressed by the explanted secondary tumor cells are then purified as described in Weidner et al., *J. of Cell Biol.* 111: 2097–2108 (1990), although other methods applicable to the present invention are well-known to the skilled artisan.

Applicants' ability to obtain high levels of HGF/SF production using the constructs of the present invention is surprising in that Rong et al., *Cell Growth & Diff*, 4: 563–569 (July 1993) show that overexpression of murine Met receptor in NIH/3T3 cells eliminated endogenous murine HGF/SF levels (Rong et al., supra at 565, Table 1B).

The level of HGF/SF production, according to the invention, is also surprising in view of the fact that the practice of the method of Blair et al., *Science* 218: 1122 (1982), without met, does not result in increased HGF/SF production. Example 8 describes the experiments that led applicants to this conclusion. FIG. 18 shows a comparison of the expression of HGF/SF in NIH/3T3 mouse fibroblast cells transfected with DNA encoding HGF/SF with HGF/SF expression in the same cells with DNA encoding Met: HGF/SF. Compared to parental NIH/3T3 cells with transfected met and HGF/SF cDNAs (FIG. 18, part A, lanes 1 and 3), significant increases in HGF/SF production occur after tumorigenesis in tumor explant cells (FIG. 18, part A, lanes 2,4 and 5). The three isotopically-labeled protein bands represent p87 (HGF/SF, uncleaved) p68α and p34β (cleaved subunits). By contrast, the dramatic amplification of HGF/SF does not occur in tumor explants when HGF/SF is present in NIH/3T3 cells without Met (FIGS. 18, part A, c.f. lane 7 to lanes 8–11).

To test further for the expression of HGF/SF, applicants used the method of reprecipitation that eliminates background and improves detection. This method is described in Rong et al. *Cell Growth and Diff.* 4: 563 (1993). These analyses show that the tumor explant cells from Met: HGF/SF tumors produce high levels of HGF/SF (FIG. 18, part B, lanes 1 and 2) while the tumors produced by HGF/SF cDNA do not (FIG. 18 part B, lanes 4 and 5). Thus, only the tumors produced with Met and HGF/SF produce high levels of HGF/SF. The expression levels of HGF/SF are clearly significantly lower when the method of Blair et al. is used without met.

In yet another embodiment, the present invention relates to three C-terminal isoforms of mouse and human Met derived from NIH/3T3 cells transfected with met cDNA. Although these isoforms most likely resulted from post-translational processing, applicants cannot exclude possible rearrangements of the transfected cDNA. Several met products truncated in the C-terminal have been reported (Prat, M., et al. *Mol. Cell. Biol.* 11: 5954–5962 (1991)) but these products are different from the isoforms according to the present invention, because they do not react with C-terminal antibodies. Moreover, these isoforms are detected only in cells expressing high levels of met, indicating that they are present in low abundance.

The present invention further contemplates the therapeutic use of Met antibodies or fragments that have been conjugated with a therapeutic agent. The objective of such immunotherapy is to deliver cytotoxic doses of radioactivity, toxin, or drug to target cells, while minimizing exposure to non-target tissues.

For example, a radioisotope can be attached to an intact antibody, or antigen-binding fragment thereof, directly or indirectly, via a chelating agent. Alternatively, immunoconjugates can be prepared in which the therapeutic agent is a toxin or drug. Useful toxins for the preparation of such immunoconjugates include ricin, abrin, pokeweed antiviral protein, gelonin, diphtherin toxin, and *Pseudomonas* endotoxin. Useful chemotherapeutic drugs for the preparation of immunoconjugates include doxorubicin, daunorubicin, methotrexate, melphalin, chlorambucil, vinca alkaloids, 5-fluorouridine, and mitomycin-C.

General techniques for preparing immunoconjugates are described, for example, by Shih et al., *Int. J. Cancer* 41:832–839 (1988), Shih et al., *Int. J. Cancer* 46:1101–1106 (1990), and Shih et al., U.S. Pat. No. 5,057,313, which are incorporated by reference.

In yet another embodiment, the present invention relates to a method of making or improving the success of growing human tumor cell xenographs in athymic nude mice. Specifically, it has been shown that Met down-regulates endogenous HGF/SF expression. Indeed, it is only by ectopic expression from an LTR that one sees ligand overexpression. Rong et al., *Cancer Res.* 53: 535 (1993). In three primary human fibroblast cell lines examined, HGF/SF is high, Met$^{hu}$ is very low. Applicants have shown that by transfection of LTR-HGF-HGF/SF cDNA into SK-LMS-1 cells, this human mesenchymal tumor cell line then expresses high levels of HGF/SF. More importantly, these transfected cells obtain the ability to grow in athymic nude mice.

Applicants have shown that autocrine receptor activation is an important factor for tumorigenesis and that murine HGF/SF has low affinity for Met$^{hu}$ but HGF/SF$^{hu}$ has a high affinity for Met$^{mu}$ as well as Met$^{hu}$. Human cells dependent on Met$^{hu}$ activation will not grow in athymic nude mice unless HGF/SF$^{hu}$ is provided. Accordingly, applicants have discovered a method of growing tumors in athymic nude mice by:

(a) transfecting LTR-HGF/SF cDNA directly into the desired Met producing cells, as taught above;

(b) by generating transgenic animals expressing HGF/SF$^{hu}$ from a transgene, according to methods well-known in the art;

(c) by substituting HGF/SF$^{hu}$ for HGF/SF$^{mu}$ through germline ES cell replacement, according to methods known in the art; and (d) by using a retroviral vector system to introduce the HGF/SF$^{hu}$ gene into the animal, pursuant to methods known in the art.

EXAMPLE 1

The c-met proto-oncogene is the receptor associated with motogenicity

The ability of HGF/SF to induce mitogenesis and/or scattering (motogenesis) in a number of human carcinoma cell lines that express c-met receptor was examined. Cell lines shown in Table 1, above, were plated in 96 well tissue culture plates at $1 \times 10^4$–$5 \times 10^4$ cells/ml and allowed to grow to near confluency. Wells were washed free of serum and cells starved for two days in serum-free media. The following day, cells were treated with either no sera, sera, or 10 ng/ml HGF/SF for 16–18 hours, and then 1 µCi of $^3$H-thymidine was added per well (5 µCi/ml) for another six hours. The assay was terminated by washing wells free of label with ice-cold PBS, fixing the cells in 5% TCA, and solubilizing the DNA with 0.25M NaOH. Samples were then counted in scintillation vials. The mitogenicity index is the ratio between thymidine incorporated in the absence of sera versus that stimulated by HGF. For motogenicity assays, cells were plated at $2 \times 10^3$/ml in 16-well chamber slides (LabTek) and grown until about 60% confluent. Cells were than washed free of serum and incubated overnight in serum-free media +/−HGF/SF (10 ng/ml). Slides were fixed with ice cold acetone for 10 minutes, stained with crystal violet (5 minutes), and rinsed well with water. Qualitative changes in "scattered phenotype" were recorded.

To demonstrate that the introduction of c-met into an epithelial cell line confers "scattering" activity onto the cells, C127 cells were transfected by lipofection (BRL) with either human met cDNA or murine met cDNA. Mitogenicity and/or motogenicity was measured as in Table 1. The results of this study are set forth in Table 2, above.

EXAMPLE 2

Production of HFG/SF in NIH/3T3 Cell Line cDNA plasmid constructs and cell lines. Met cDNA plasmids were constructed in pMB1, a derivative (without the polylinker sequences) of pMEX, Oskam, R., et al. *Proc. Nat'l. Acad. Sci., U.S.A.* 85: 2964–2968 (1988); that contains the long terminal repeat (LTR) promoter from Moloney murine sarcoma virus (MSV) and the polyadenylation signal of simian virus 40. The met$^{hu}$ plasmid was constructed by replacing an internal 300-bp EcoRI fragment with the 250-bp EcoRI fragment of pOK in the 4.6 Kb met$^{hu}$ sequence containing the open reading frame. Park, M., et al. *Proc. Nat'l. Acad. Sci. U.S.A.* 84: 6379–6383 (1987); Rodriguez et al., *Mol. Cell Biol.* 11: 2962–2970 (1991). The met$^{mu}$ plasmid contains the entire 4.6-Kb mouse met open reading frame. Iyer, A., et al. *Cell Growth & Diff.* 1:87–95 (1990). Chimeric human/mouse met constructs were made using the conserved PvuII site (amino acid 807). A HGF$^{hu}$ plasmid was constructed by inserting the 2.3 kb BamH1-KpnI fragments of the human HGF sequence into the BamH1-KpnI sites of pMEX. Nakamura, T., et al. *Nature* 342: 440–443 (1989); Oskam, R., et al. *Proc. Nat'l. Acad. Sci., U.S.A.* 85: 2964–2968 (1988). NIH/3T3 490 cells were grown in DMEM (Gibco) with 8% calf serum (Gibco).

DNA transfection. The calcium phosphate method of DNA transfection (Cooper, C. S., et al. *Nature* 311:29–33 (1984)) was carried out by mixing plasmid DNA (2 µg in 75 µl of water containing 8 µg of calf thymus carrier DNA) with 75 µl of 0.67M CaCl$_2$. This mixture was added dropwise to 0.15 ml of solution H (0.27M NaCl, 0.01M KCl, 0.0014M Na$_2$HPO$_4$.7H$_2$O, 0.012M dextrose) with continuous agitation. After remaining at room temperature for 30 minutes, the mixture was added to cells having about 70% confluence on a 35-mm dish containing 1 ml medium with 0.01M Hepes buffer. Cells were incubated at 37° C. for 4 hours, then treated with 15% glycerol (v/v) in solution H for 2 minutes. For G418 selection, cells were re-fed with DMEM and 8% calf serum overnight and subsequently transferred to three 60 mm dishes. After 24 hours incubation, cells were fed with medium containing 400 µg/ml G418 (Gibco) twice a week.

Northern analysis. RNA was isolated using RNAsol (CINNA/BIOTECX). Twenty micrograms of RNA was subjected to electrophoresis on 1% denaturing formaldehyde agarose gels followed by transfer to nitrocellulose filters (Schleicher and Schuell). Blots were hybridized at 42° C. for 15 hours to $^{32}$P-labeled randomly primed DNA probes (10$^9$ cpm/µg) in 30% formamide, 6×saline sodium citrate (SSC), 5×Denhardt's solution, 50 mM sodium phosphate (pH 6.8), and sonicated salmon sperm DNA (250 µg/ml). After hybridization, filters were washed twice in 1×SSC and 0.1% SDS at room temperature and in 1×SSC and 0.1% SDS at 50° C. Filters were dried and exposed to X-ray films for 1–3 days at −70° C.

Immunoprecipitation. Near-confluent cells were labeled with 0.25 mCi of Translabel (ICN) (1 ml/35-mm dish) for 4 to 6 hours in DMEM lacking methionine and cysteine (Gibco). The labeled cells were lysed in 0.5 ml of RIPA buffer [1% Triton X-100, 1% sodium deoxycholate, 0.1% sodium dodecylsulfate (SDS), 0.15M NaCl, 0.02M NaPO$_4$, pH 7.2, 1 mM phenylmethylsulfonyl fluoride (PMSF), 2 mM EDTA, 50 mM NaF, 30 mM sodium pyrophosphate]. Clarified lysates having equal radioactive counts were immunoprecipitated with 19S monoclonal anti-met antibody, Faletto, D. L. et al. *Oncogene* 7: 1149–1157 (1991) at 4° C. overnight. Immunoprecipitates were complexed to protein G-sepharose (Gibco), then washed twice with RIPA buffer and high-salt buffer (1M NaCl, 10 mM Tris-HCl, pH 7.2, 0.5% Triton). The immunocomplexes were solubilized by boiling in SDS sample buffer in the presence of 5% β-mercaptoethanol. Samples were analyzed by SDS-polyacrylamide gel electrophoresis followed by treatment with fluorographic enhancer (Amplify™, Amersham) and fluorography with an intensifying screen at −70° C.

SP260 is a peptide antibody made from rabbit antisera, directed against the C-terminal 21 amino acids of $met^{mu}$. (Iyer, A., et al. *Cell Growth & Diff.* 1: 87–95 (1990)). A3.1.2 is an anti-human recombinant HGF monoclonal antibody (IgG, subclass G2a).

Pulse chase analysis. Near-confluent cells were labeled for 45 min with 0.25 mCi of Translabel in 1 ml (per 35-mm dish) DMEM lacking methionine and cysteine. The cells were washed twice and chased with complete medium for 3 hours, then lysed and subjected to immunoprecipitation analysis.

Surface iodination. Near-confluent cells were labeled with Na $^{125}$I in the presence of Iodo-Gen (Pierce). Twenty microliters of the Iodo-Gen reagent (10 mg/ml in chloroform) was added to the bottom of a I-dram vial and dried with a stream of nitrogen. The Iodo-Gen was then dissolved in 1M Tris with 10 mM EDTA (pH 7.5) and added to the cell pellet. Na $^{125}$I (0.5 mCi) was added to the reaction for 10 minutes. The labeled cells were washed three times with PBS, then lysed with RIPA buffer and subjected to immunoprecipitation analysis.

Western analysis. Near-confluent cells on a 100-mm dish were washed twice with cold TBS (10 mM Tris pH 8.0, 150 mM NaCl) and lysed in 1 ml of lysis buffer (25 mM Tris-HCl, pH 8.0, 100 mM NaCl, 50 mM NaF, 1% Triton X-100, 10 μg/ml aprotinin, 10 μg/ml leupeptin, 1.25 mM PMSF, 1 mM vanadate). One milligram of protein was immunoprecipitated with anti-C28 anti-Met$^{hu}$ polyclonal antibody (Gonzatti-Haces, M. et al., *Proc. Nat'l. Acad. Sci. U.S.A.*, 85: 21–25 (1988)) and subjected to Western analysis with either anti-phosphotyrosine (anti-P-Tyr) antibody, 4G10 (Morrison, D. K., et al., *Cell*, 58: 649–657(1989)), or human or mouse met-specific antibodies, 19S monoclonal (Faletto, D. L., et al., *Oncogene* 7: 1149–1157 (1991)) or SP260 (Iyer, A., et al., *Cell Growth & Diff.* 1: 87–95 (1990)), respectively. $^{125}$I-protein A (Amersham) was used to detect positive bands according to the manufacturer's instructions.

Nude mouse tumor assay. The assay was performed as previously described (Blair, D. G., et al., *Science* 218: 1122–1125 (1982)). Transfected and G418 selected NIH/3T3 cells (10$^6$) were washed twice and resuspended in 0.1 ml of serum-free medium. The cells were injected onto the back of weanling athymic nude mice (Harlan Sprague Dawley, Inc.). Tumor formation was monitored each week for up to 10 weeks. Tumors were explanted when they reached 15 mm in size, and the tumor cells were subjected to immunoprecipitation analysis.

Soft-agar assay. Soft-agar growth assay was carried out by modification of Blair et al., *Virology* 95: 303–316 (1979). Briefly, trypsinized cells were suspended at 2×10$^5$ and 2×10$^4$ cells in 8 ml of DMEM (Gibco) with 10% calf serum and 0.24% purified agar (DIFCO) and quickly transferred to a duplicate 60-mm dish containing a hardened base layer of DMEM with 10% calf serum and 0.27% agar. Plates were fed with 2 ml of DMEM with 10% calf serum and 0.27% agar at weekly intervals. Colonies were counted microscopically after 3 weeks incubation at 37° C.

Figure 1A:
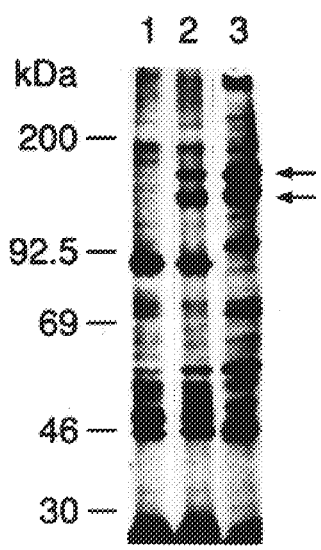
FIGS. 1A–C, demonstrates met products in transfected NIH/3T3 cells. Panel (A) Immunoprecipitation analysis. Cells were metabolically labeled with [$^{35}$S]methionine and [$^{35}$S]cysteine (Translabel, ICN) for 5 hours in DMEM lacking methionine and cysteine (Gibco) and cell lysates were immunoprecipitated with either a Met$^{hu}$-specific C-terminal monoclonal antibody, 19S (Faletto, D. L. et al., *Oncogene* 7: 1149–1157 (1991) (lanes 1 and 2), or Met$^{mu}$-specific peptide antibody, SP260 (Iyer, A. et al., *Cell Growth & Diff.* 1: 87–95 (1990)) (lane 3). Immunoprecipitation was completed with protein G-sepharose (Gibco), the complex was solubilized in SDS sample buffer with 5% β-mercaptoethanol, and resolved on 7.5% acrylamide gels. In lane 1, cells were transfected with pSV2neo only; in lane 2, cells were transfected with met$^{hu}$; in lane 3, cells were transfected with met$^{mu}$. Panel B Pulse-chase analysis. Cells were metabolically labeled with [$^{35}$S]methionine and [$^{35}$S] cysteine for 45 minutes (lanes 1 and 3), followed by a chase period of 3 hours (lanes 2 and 4). Met was immunoprecipitated with 19S monoclonal antibody against Met$^{hu}$ (lanes 1 and 2) or SP260 peptide antibody, against Met$^{mu}$ (lanes 3 and 4) and subjected to electrophoresis as in panel A. In lanes 1 and 2 are cells transfected with Met$^{hu}$; in lanes 3 and 4 are cells transfected with Met$^{mu}$. Panel (C) Cell surface iodination of met. Near-confluent cells were pelleted and labeled with Na$^{125}$I in the presence of Iodo-Gen (Pierce). The labeled cells were washed three times with PBS, lysed with RIPA buffer, and subjected to immunoprecipitation with either 19S monoclonal antibody (lanes 1 and 2) or SP260 peptide antibody (lanes 3 and 4). Met$^{hu}$ expressing NIH/3T3 cells are in lanes 1 and 3. Met$^{mu}$ expressing NIH/3T3 cells are in lanes 2 and 4. Arrows indicate the positions of p170$^{met}$ and p140$^{met}$.
Figure 1B:
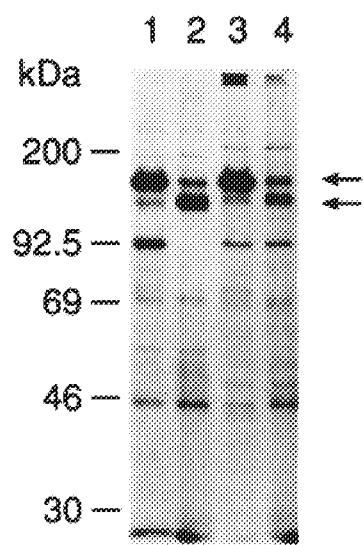
Figure 1C:
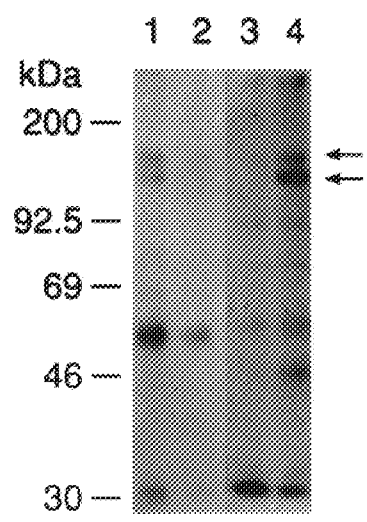
Figure 2A:
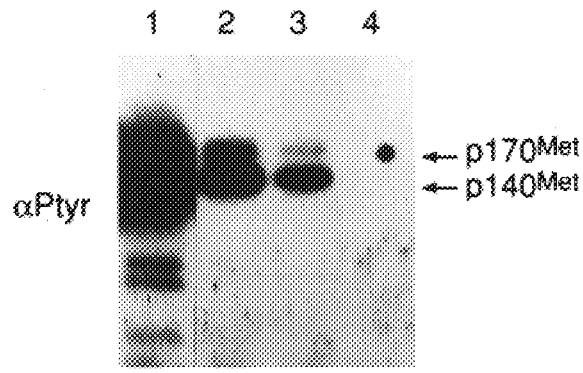
FIGS. 2A–D, shows met product reactivity with anti-P-Tyr antibody. Near-confluent cells on a 100-mm dish were washed twice with cold TBS and lysed in 1 ml of lysis buffer (25 mM Tris-HCl, pH 8.0, 100 mM NaCl, 50 mM NaF, 1% Triton X-100, 10 μg/ml aprotinin, 10 μg/ml leupeptin, 1.25 mM PMSF, 1 mM sodium orthovanadate). One milligram of protein was immunoprecipitated with anti-C28 peptide antibody for Met$^{hu}$, (Gonzatti-Haces, M. et al. *Proc. Nat'l. Acad. Sci. U.S.A.* 85: 21–25 (1988)) (panels A and C) or peptide antibody SP260 for Met$^{mu}$ (Iyer, A., et al., *Cell Growth & Diff.* 1: 87–95 (1990)) (panels B and D). After dissolving in SDS buffer, samples were separated by SDS-PAGE on 7.5% gels, transferred to Immobilon-P (Millipore), and probed with anti-P-Tyr antibody, 4G10, Morrison, D. K., et al., *Cell* 58: 649–657 (1989) (panels A and B), 19S monoclonal antibody (panel C), or mouse met peptide antibody, SP260 (panel D). The Immobilon filter was then incubated with $^{125}$I-protein A (ICN) and subjected to autoradiography. Lanes 1–3 of panels A and C have three different lines of met$^{hu}$-transfected cells; lane 4 has NIH/3T3 control cells. Lane 1 of panels B and D are cells transfected with met$^{mu}$. Lane 2 has NIH/3T3 control cells.
Figure 2B:
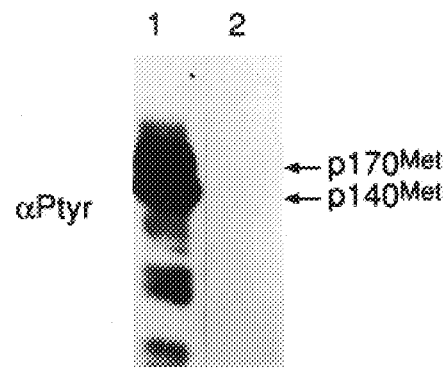
Figure 2C:
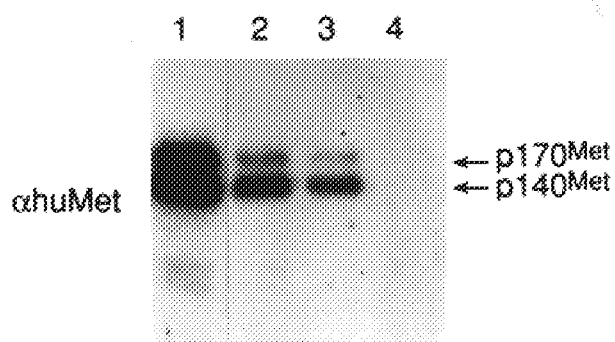
Figure 2D:
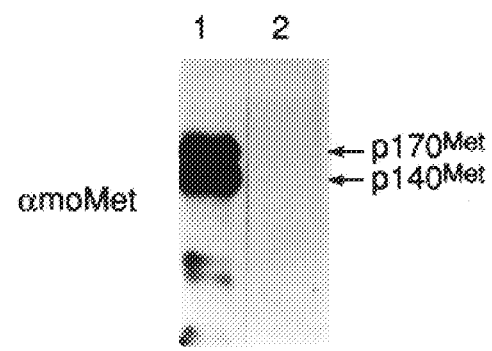

Expression of Met$^{hu}$ and Met$^{mu}$ in NIH/3T3 cells. Plasmids containing met$^{hu}$ proto-oncogene cDNA were cotransfected with pSV2neo into NIH/3T3 cells and G418-resistant cells were screened for human or mouse Met expression by immuno-precipitation analyses. These analyses show that both human and mouse p170$^{met}$ and p140$^{met}$ are expressed in transfected NIH/3T3 cells (FIG. 1, part A, lanes 2 and 3, respectively). Similar levels of met$^{mu}$ expression in NIH/3T3 cells has been reported (Iyer, A., et al., *Cell Growth & Diff.* 1:87–95 (1990)). Applicants found little or no expression of the endogenous Met$^{mu}$ in the G418-resistant cells expressing Met$^{hu}$. Appropriate processing of Met$^{hu}$ and Met$^{mu}$ was examined by pulse-chase labeling experiments and these studies showed that p170$^{met}$ synthesized during a 45 minute pulse (FIG. 1, part B, lanes 1 and 3) was efficiently processed after 3 hours into the mature p140$^{met}$ (lanes 2 and 4). Moreover, human and mouse Met were localized on the cell surface. Applicants labeled intact cells with Na$^{125}$I and immunoprecipitation of the lysates showed that both forms, p140$^{met}$ and p170$^{met}$ were iodinated (FIG. 1, part C). Thus, human or mouse Met expressed in NIH/3T3 cells is correctly processed and localized on the cell surface. These analyses also show that p170$^{met}$ arrives at the cell surface uncleaved. The iodination of p170$^{met}$ did not result from lysed cells, since under similar iodination conditions the cytoplasmic tpr-met oncoprotein was not detected. (Gonzatti-Haces, M., et al., *Proc. Nat'l. Acad. Sci. U.S.A.* 85: 21–25 (1988)). Furthermore, p170$^{met}$ expressed in Okajima cells, a human gastric carcinoma cell line that overexpresses met$^{hu}$ is also labeled by surface iodination, but the ratio of p170$^{met}$ to p140$^{met}$ labeled was less when compared with NIH/3T3 cells.

Constitutive tyrosine phosphorylation of met in NIH/3T3 cells. By Northern hybridization analyses, applicants detected HGF/SF mRNA expression in NIH/3T3 cells and in cells transfected with either met$^{hu}$ or met$^{mu}$. Applicants observed the same level of HGF/SF mRNA expression, suggesting that overexpression of met$^{hu}$ or met$^{mu}$ in the G418 selected lines did not affect endogenous HGF/SF expression. These results also suggested that Met might be activated in an autocrine fashion. Therefore, applicants examined whether the Met$^{hu}$ and Met$^{mu}$ expressed in these cells reacted with anti-P-Tyr antibody. Extracts from cell lines expressing Met$^{hu}$ and Met$^{mu}$ were subjected to immunoprecipitation with human- or mouse-specific peptide antibodies followed by Western analyses using either anti-P-Tyr antibody (FIG. 2, parts A and B), or human (FIG. 2, part C), or mouse-specific (FIG. 2, part D) Met antibody. These analyses show that both p170$^{met}$ and p140$^{met}$ of Met$^{hu}$ and Met$^{hu}$ reacted strongly with anti-P-Tyr antibody. This is the first example demonstrating tyrosine phosphorylation of p170$^{met}$ react with anti-P-Tyr antibody. One line expressed Met$^{hu}$ at very high levels (FIG. 2, parts A and C, lane 1). This was an exception since all other Met$^{hu}$ lines expressed levels comparable to lines analyzed in FIG. 2, parts A and C, lanes 2 and 3. Additional C-terminal Met protein products (p85, p75, and p65) were detected with C-terminal antibodies in cells expressing either mouse or human met (FIG. 2, parts A–D, lane 1).

Tumorigenicity of met in NIH/3T3 cells. Applicants observed that NIH/3T3 cell cultures expressing Met$^{mu}$, but not Met$^{hu}$, were transformed (Iyer, A., et al., *Cell Growth & Diff.* 1: 87–95 (1990)) as shown in FIG. 5. This was confirmed by testing for their tumorigenicity in nude mice following transfection and G418 selection. NIH/3T3 cells expressing met$^{mu}$ were highly tumorigenic as shown in Table 3, below, while cells expressing met$^{hu}$ were low in tumorigenicity and only in one line out of eight tested produced tumors.

TABLE 3

Tumorigenicity of NIH/3T3 Cells Transfected
With met$^{hu}$ or met$^{mu}$ cDNA

| Transfected genes | Mice with tumors/ No. tested | Latency (weeks) |
|---|---|---|
| neo$^r$ | 0/8 | |
| neo$^r$, met$^{hu}$ | 2/23 | 5 |
| neo$^r$, met$^{mu}$ | 12/12 | 3–5 |

Cells (10$^6$) expressing transfected genes were washed twice with serum-free medium and injected subcutaneously on the back of weanling athymic nude mice. Tumor formation was monitored each week up to 10 weeks.

These tumorigenic lines, before injection, produced high levels of Met$^{hu}$ (FIG. 2, parts A and C, lane 1) compared to lines that were not tumorigenic (FIG. 2, parts A and C, lanes 2 and 3). The tumor explants of this line displayed even higher levels of Met$^{hu}$. The levels of a Met$^{mu}$ line before injection is shown for comparison (FIG. 2, parts B and D, lane 1). Cell lines expressing lower levels of Met$^{mu}$ are also tumorigenic in this assay. The two tumors generated by line 123-1 (Table 3) showed increased levels of endogenous Met$^{mu}$ expression and reduced levels of Met$^{hu}$, suggesting that they may have arisen through mouse met amplification as previously described. Cooper, C. S., et al., *EMBO J.* 5: 2623–2628 (1986); Heldin, C.-H. et al., *Eur. J. Biochem.* 184: 487–496 (1989). Applicants conclude that Met$^{hu}$ is poorly tumorigenic in NIH/3T3 cells.

Tumorigenicity of NIH/3T3 cells cotransfected with met$^{hu}$ and HGF/SF$^{hu}$. One explanation for the low tumorigenicity of met$^{hu}$- transfected NIH/3T3 cells is that met$^{hu}$ receptor activation by endogenous HGF/SF$^{mu}$ may not provide sufficient signal. Applicants therefore tested whether transfection of both met$^{hu}$ and HGF/SF$^{hu}$ cDNAS would increase tumorigenicity through an autocrine mechanism. These analyses show that NIH/3T3 cells cotransfected with met$^{hu}$ and HGF/SF$^{hu}$ are highly tumorigenic (Table 4).

TABLE 4

Tumorigenicity of NIH/3T3 Cells Transfected
With met$^{hu}$ ± HGF/SF$^{hu}$ cDNAs

| Transfected genes | Mice with tumors/No. tested | Latency (weeks) |
|---|---|---|
| neo$^r$ | 0/6 | — |
| neo$^r$, met$^{hu}$ | 0/6 | — |
| neo$^r$, met$^{hu}$, HGF$^{hu}$ | 17/19 | 4–6 |
| neo$^r$, HGF$^{hu}$ | 3/7 | 7 |

Figure 3A:
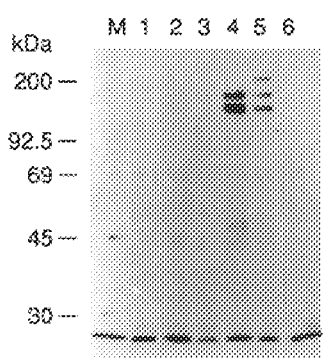
FIGS. 3A–C, shows the characterization of Met$^{hu}$ and HGF/SF$^{hu}$ in NIH/3T3 tumor cells. Tumor cells were explanted and metabolically labeled with [$^{35}$S]methionine and [$^{35}$S]cysteine for 6 hours. Cell lysates were immunoprecipitated with either 19S monoclonal antibody (panel A), or peptide antibody SP260 (panel B). Then, 0.25 ml of the "6 hour" supernatants was concentrated threefold in Centricon (Amicon; 10K cut-off); the volumes were adjusted to 0.3 ml with RIPA buffer and the samples were immunoprecipitated with anti-HGF monoclonal antibody A3.1.2 (panel C). Lanes 1 and 3 are samples from two different lines of cotransfected cells before injection. Lane 2 is a tumor explant derived from the cells analyzed in lane 1; lanes 4 and 5 are tumor explants derived from the cells analyzed in lane 3. Lane 6 is a sample prepared from control NIH/3T3 cells. Arrows indicate the positions of p170$^{met}$ and p140$^{met}$ (panels A and B) and the positions of the 87 kDa (the precursor), 69 kDa, and 34 kDa HGF polypeptides (panel C).
Figure 3B:
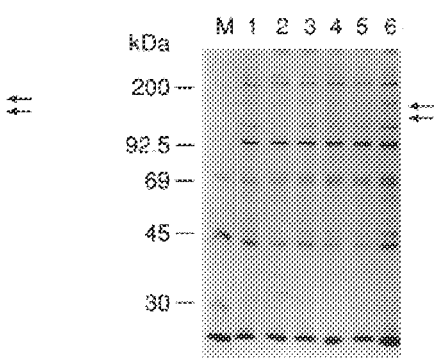
Figure 3C:
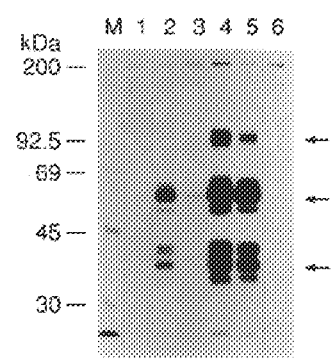

Moreover, the tumor cells showed increased levels of both Met$^{hu}$ and HGF/SF$^{hu}$ (FIG. 3, parts A and C, respectively; lanes 2, 4, and 5). In the tumor explants characterized in lanes 4 and 5, high levels of both Met$^{hu}$ and HGF/SF$^{hu}$ are expressed. None of the cell lines showed amplification of endogenous met$^{mu}$ (FIG. 3, part B). Applicants found that HGF/SF$^{hu}$-transfected NIH/3T3 cells also produced several tumors, but the levels of HGF/SF$^{hu}$ product expressed in tumor cells derived from explants was not as high as the levels expressed in tumors from the met$^{hu}$-HGF/SF$^{hu}$ cotransfection experiments (FIG. 3, part C). In one out of five HGF/SF$^{hu}$ tumors, elevated levels of endogenous met$^{hu}$ was detected.

Figure 4:
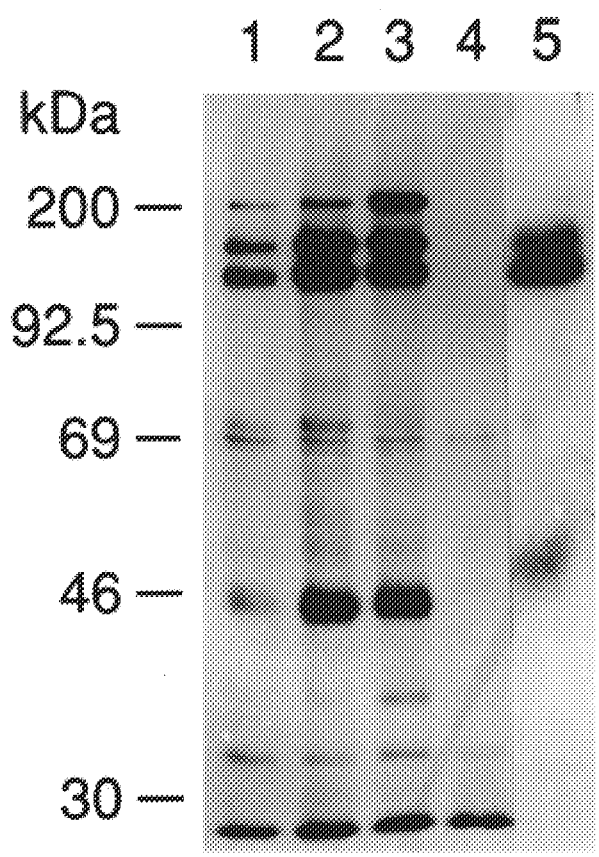
FIG. 4 demonstrates the characterization of Met chimeric protein in NIH/3T3 cell tumors. Cells were metabolically labeled with [$^{35}$S]methionine and [$^{35}$S]cysteine for 6 hours and cell lysates were immunoprecipitated with 19S monoclonal antibody (lanes 1–4). In lane 1 are uninjected G418 (Gibco)-resistant cells transfected with mouse N-terminal/human C-terminal chimeric met; in lanes 2 and 3 are tumors derived from cells analyzed in lane 1; in lane 4, NIH/3T3 control cells; in lane 5, Western blot of the same cells as in lane 1, analyzed with anti-P-Tyr antibody (4G10) following immunoprecipitation with human anti-C28 peptide antibody.

Tumorigenicity of chimeric human/mouse met in NIH/3T3 cells. To test whether the ligand binding domain influenced tumorigenicity, applicants generated chimeric human/mouse met receptor molecules and tested their tumorigenicity in nude mice (FIG. 5). Applicants used a conserved PvuII site in the external domain adjacent to the transmembrane coding sequences to make these recombinants. It was found that when the mouse external ligand-binding domain was linked to the human transmembrane and tyrosine kinase domains, the chimeric receptor displayed tumorigenic activity equivalent to that of the Met$^{mu}$ (FIG. 5). Explants of these tumors showed an increased level of chimeric Met protein that was recognized with human antibody directed against the human tyrosine kinase domain (FIG. 4, lanes 2 and 3). No evidence for met$^{mu}$ amplification was observed in these tumors, and the chimeric product was recognized by Western analysis with anti-P-Tyr antibody (FIG. 4, lane 5).

In contrast to the high tumorigenicity of the chimera with the mouse Met external ligand-binding domain, the reciprocal human N-terminal/mouse C-terminal chimera was poorly tumorigenic. However, as with the Met$^{hu}$, when this chimera was cotransfected with HGF/SF$^{hu}$ cDNA, efficient tumor formation was observed (FIG. 5). Applicants also show that cells expressing the met$^{mu}$-met$^{hu}$ chimera, before injecting into nude mice, are transformed and form colonies in soft agar like met$^{hu}$-transfected cells. The met$^{hu}$-met$^{mu}$ cells do not display a transformed phenotype unless coexpressed with HGF/SF. Applicants concluded that the Met$^{mu}$ external ligand-binding domain is a major factor in determining tumorigenicity.

EXAMPLE 3

Met and HGF/SF expression in human fibroblast cell cultures and sarcoma cell lines Cell lines and antibodies. Cell lines used in this study are listed in FIG. 21. Most of the cell lines used in this study were obtained from American Type Culture Collection (ATCC) and grown as recommended. A fibrosarcoma cell line, 8387 (grown in DMEM with 10% bovine fetal serum), and a rhabdomyosarcoma cell line, RD-1 (grown in McCoy's 5A with 15% bovine fetal serum), were obtained from Doug Halverson (NCI, Frederick, Md.). NIH/3T3 cells transfected with neo$^r$ and human met (met$^{hu}$) were described by Rong et al. (*Mol. Cell Biol.* 12: 5152 (1992)).

The 19S anti-Met monoclonal antibody was generated against a bacterially-expressed p50 form of Met$^{hu}$. (Faletto et al., *Oncogene* 7: 1149 (1991); Rong et al., *Mol. Cell. Biol.* 12: 5152 (1992)). The Met-specific C28 anti-peptide antibody was raised by immunization of rabbits with the 28 amino acid C-terminal peptide of human Met. (Gonzatti-Haces et al. *Proc. Nat'l. Acad. Sci. U.S.A.* 85: 21 (1988)). A3.1.2 is a monoclonal antibody against human recombinant HGF. (Rong et al., *Mol. Cell. Biol.* 12: 5152 (1992)). 23C2 is a monoclonal antibody against human placental SF. (Bhargava et al., *Cell Growth & Diff.* 3: 11 (1992)). Anti-rhHGF-1 is a rabbit polyclonal antibody against human recombinant HGF. (Montesano et al., *Cell* 67: 901 (1991)). Anti-rhHGF-2 is purified goat IgG against human recombinant HGF (R&D Systems). 4G10 is a monoclonal phospho-tyrosine antibody (anti-P-Tyr). (Morrison et al., *Cell* 58: 649 (1989)).

Immunoprecipitation analysis. Immunoprecipitation analysis for both Met and HGF/SF was carried out as described previously. (Rong et al., *Mol. Cell. Biol.* 12: 5152 (1992)).

Confocal laser scan microscopy (CLSM) and immunofluorescence analysis. Immunofluorescence assays were performed as described previously. (Rong et al., *Cell Growth & Diff.* 4: 563 (1993); Tsarfaty et al., *Science* 257: 1258 (1992)).

Western immunoblot analysis. Western analysis was performed essentially as described previously (Rong et al., *Mol. Cell. Biol.* 12: 5152 (1992)), except that the cells were lysed in RIPA buffer [1% Triton X-100, 1% sodium deoxycholate, 0.1% SDS, 0.15M NaCl, 0.02M NaPO$_4$ (pH 7.2)], containing 1.25 mM PMSF, 2 mM EDTA, 50 mM NaF, 30 mM Na pyrophosphate, 10 μg/ml aprotinin, 10 μg/ml leupeptin, 1 mM Na ortho-vanadate.

Scatter assay. Scatter assay using MDCK cell line was carried out as described previously. (Rong et al., *Cell Growth & Diff.* 4: 563 (1993); Stoker et al., *Nature* 327: 239 (1987)).

Northern analysis. Total cellular RNA was isolated using RNAzol as described by the supplier (CINNA/BIOTECX). Twenty μg of total RNA was denatured, electrophoresed on 1% formaldehyde agarose gel, and transferred to nylon membranes (Schleicher and Schuell) as described. (Iyer et al., Cell Growth & Diff. 1: 87 (1990)). Hybridizations were carried out for two days with $10^6$ cpm/ml of probe (specific activity $10^8$ cpm/μg) (Random Priming Labeling Kit, Boehringer-Mannheim). Filters were washed twice in 2×SSC-0.1% SDS at room temperature for 10 min and then three times in 0.2×SSC-0.1% SDS at room temperature for 10 min and then three times in 0.2×SSC-0.1% SDS at 55° C.

Met and HGF/SF expression. Samples of total RNA were extracted from non-immortalized human fibroblast cell cultures and from human cell lines established from various human sarcomas and analyzed for met RNA expression using a full-length met cDNA probe. The major met mRNA, a 9 kb transcript (Park, M., et al., *Cell* 45: 895 (1986)), was present in all of the samples tested (FIG. 10 (panel A) and FIG. 21). Thus, human cell lines established from various sarcomas express high level of activated Met receptor.

These cells and cell lines also were examined for Met protein expression by immunoblot analysis. Met was precipitated from cell lysates using C28 anti-peptide antibody directed against the C-terminus of the human Met. (Gonzatti-Haces et al., *Proc. Nat'l. Acad. Sci. U.S.A.* 85: 21 (1988)).

The immunoprecipitates were subjected to SDS-PAGE, followed by immunoblot analysis using the 19S monoclonal antibody, directed against the intracellular Met domain (FIG. 10 (panel B)). (Faletto et al., *Oncogene* 7: 1149 (1991); Rong et al., *Mol. Cell. Biol.* 12: 5152 (1992)). Low levels of Met protein, p140$^{Met}$ and its precursor p170$^{Met}$, were detected in several of the primary fibroblast cultures (FIG. 10 (panel B; band a; lanes 1 and 8) and FIG. 21), but much higher levels were present in many of the human sarcoma cell lines tested (FIG. 10 (panel B; band a; lanes 2, 4–7 and 9–11) and FIG. 21). These levels were similar to the high levels of Met protein observed n NIH/3T3 cells transformed by Met. (Rong et al., *Mol. Cell. Biol.* 12: 5152 (1992)).

These analyses also showed that there was no direct correlation between the level of met mRNA detected (FIG. 10, panel A) and the level of Met protein expressed (FIG. 10, panel B (band a)). For example, the levels of met mRNA detected in 8387 and Saos-2 cells were higher than the levels detected in HT1080 cells; however, the HT1080 cells express higher levels of Met. Likewise, equivalent amounts of met RNA were detected in Hems and HT1080, but the level of Met in the Hems fibroblasts was barely detectable (FIG. 10, panel B (band a)). These results showed significant variation in the regulation of Met protein expression, although the difference in steady-state Met levels also may reflect ligand-mediated down-modulation of the receptor. The high levels of Met in the sarcoma cell lines and the presence of Met in fibroblast cells represented novel findings, since Met expression was thought to be preferentially present in epithelial cells, while only the ligand was restricted to mesenchymal cells. (Birchmeier et al., *Bio Essays* 15: 1 (1993); Gherardi et al., *Met. Cancer Cells* 3: 227 (1991)).

The levels of immunoprecipitable HGF/SF were determined using growth medium harvested from metabolically labeled fibroblast and sarcoma cells (FIG. 10, panel C). Abundant levels of the HGF/SF p69 a-subunit (p69$^{HGF/SF}$) were observed in all of the primary fibroblast cell cultures (FIG. 10, panel C, lanes 1–3; FIG. 21), but only one sarcoma cell line (Hs913T) secreted high levels (FIG. 10, panel C, lane 12). The level of HGF/SF also was determined by scatter assays performed on growth medium that was conditioned on confluent cells for 72 hrs. Comparable to the high levels of p69$^{HGF/SF}$ detected, high levels of scatter activity were detected in conditioned media from HEL299 and Hems fibroblast cultures (FIG. 21). However, lower activity was observed in the scatter assays performed with Hs68 and Malme-3 conditioned medium that did not correlate with the high levels of p69$^{HGF/SF}$ detected (FIG. 21; FIG. 10, panel C, lane 3). The Hs913T fibrosarcoma cells also express high levels of p69$^{HFG/SF}$ (FIG. 10, panel C, lane 12), and also exhibit low scatter activity. However, with the exception of Hs913T cells, the levels of HGF/SF and scatter activity were low in cells that expressed high levels of Met (FIG. 21). A similar marked reduction in the endogenous HGF/SF was observed in NIH/3T3 cells overexpressing mouse Met (Met$^{mu}$) that was presumably due to the depletion of the ligand by the receptor. (Rong et al., *Cell Growth & Diff.* 4:563 (1993)). Evidence for the HGF/SF receptor activation was indicated by the high reactivity of Met$^{mu}$ with anti-phosphotyrosine (anti-P-Tyr) antibody.

Anti-P-Tyr immunoblot analyses on the Met expressed in the human fibroblast cell cultures and in the sarcoma cell lines (FIG. 10, panel B (band b)) showed that, in general, the overexpressed Met is highly reactive with anti-P-Tyr antibody (FIG. 10, panel B (band b; lanes 2 and 4–6, 9 and 10); FIG. 21), similar to Met$^{mu}$ in NIH/3T3 cells. (Rong et al., *Mol. Cell. Biol.* 12: 5152 (1992)). Met$^{hu}$ was weakly reactive with anti-P-Tyr antibody in the primary Hems fibroblasts (FIG. 10, panel B (band b; lane 1), suggesting that the receptor was activated in an autocrine fashion by endogenous HGF/SF.

EXAMPLE 4

Autocrine interaction of Met and HFG/SF in primary fibroblast cells

Experiments were performed to test the possibility that an autocrine Met-HGF/SF stimulatory pathway exists in the primary fibroblast cell cultures. Hems and HEL299 cells expressed low levels of Met and high levels of HGF/SF compared to other cells lines tested (FIG. 10, panel B). To test whether the level of Met was being down-modulated by HGF/SF, anti-rhHGF-1, a neutralizing HGF/SF antibody (Montesano et al., *Cell* 67: 901 (1991)), was added to the growth medium of HEL299 and Hems cells. After 48 hrs, cell lysates were analyzed for levels of Met by immunoblot analysis (FIG. 11).

The results of these studies indicate that there is a significant increase in the amount of p140$^{Met}$ in HEL299 cells (FIG. 11, lanes 1–4) and Hems cells (FIG. 11, lanes 5–6) in the presence of the antibody. Therefore, these analyses indicate Met is down-regulated via extracellular-autocrine activation. The requirement for HGF/SF to be activated by extracellular proteolytic cleavage was consistent with these results. (Miyazawa et al., *J. Biol. Chem.* 268: 10024 (1993); Naka et al., *J. Biol. Chem.* 267: 20114 (1992)).

EXAMPLE 5

Mitogenic response of sarcoma cells to HFG/SF

Mitogenic assay. $3 \times 10^3$ cells were seeded into 96-well microtiter plates (Costar). After overnight incubation at 37° C., these cells were starved in serum-free medium for two days. Different concentrations of purified human HGF (HGF/SF) (Rong et al., *Cell Growth & Diff.* 4: 563 (1993)) were added in the presence or absence of $HGF^{hu}$ neutralizing antibody (anti-rhHGF-2, R&D Systems, 1:20 dilution) and incubated overnight. $^3$H-thymidine was added at 1 $\mu$Ci/well for 4 h and cells were lysed with 0.1 ml of 0.02M NaOH-0.1% SDS. Aliquots of the lysate were used for scintillation counting.

Mitogenic response to HGF/SF. Met-HGF/SF signalling has been implicated in both mitogenic and motogenic activities for epithelial cells. (Gherardi et al., *Met. Cancer Cells* 3: 227 (1991)). As a control for HGF/SF mitogenicity, $^3$H-thymidine incorporation was measured in NIH/3T3 cells overexpressing $Met^{hu}$ (Rong et al., *Mol. Cell. Biol.* 12: 5152 (1992)) in response to the addition of exogenous $HGF/SF^{hu}$ (FIG. 12). A nine-fold stimulation of $^3$H-thymidine incorporation was observed when 5 units/ml of exogenous HGF/SF was added to NIH/3T3 cells overexpressing $Met^{hu}$ (FIG. 12, panel B), but not to control NIH/3T3 cells (FIG. 12, panel A). These analyses showed that $HGF/SF^{hu}$ was mitogenic for NIH/3T3 fibroblast cells overexpressing $Met^{hu}$ but, at high levels, the ligand was inhibitory.

HGF/SF also stimulated $^3$H-thymidine incorporation in the human sarcoma cell line SK-LMS-1 (FIG. 12, panel C) and this stimulation was prevented by the addition of anti-rhHGF-2 neutralizing antibody (FIG. 12, panel D). Curiously, much higher levels of $HGF/SF^{hu}$ (16x) were required for stimulation of the SK-LMS-1 cells compared to NIH/3T3 cells overexpressing $Met^{hu}$. Two other cell sarcoma cell lines, HOS and RD, also showed increased $^3$H-thymidine incorporation in response to 80–120 units/ml HGF/SF, while SK-UT-1 and U-205 cells did not respond even through the cells express $Met^{hu}$ and HGF/SF was not detected (FIG. 21). Thus, $HGF/SF^{hu}$ can elicit a mitogenic signal in sarcoma cells expressing the Met receptor. The low (or lack of) response to HGF/SF in the sarcoma cells suggested the presence of an inhibitor or mutation that interrupts Met signaling.

EXAMPLE 6

The expression of Met and HFG/SF in human primary tumors

Figure 13A:
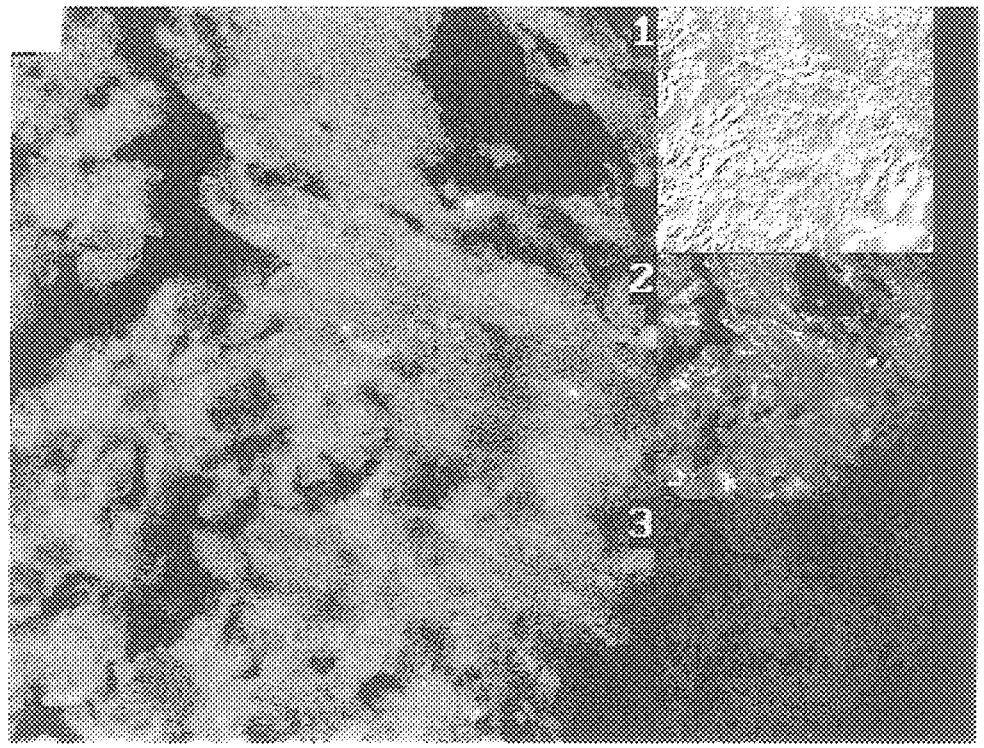
Figure 13B:
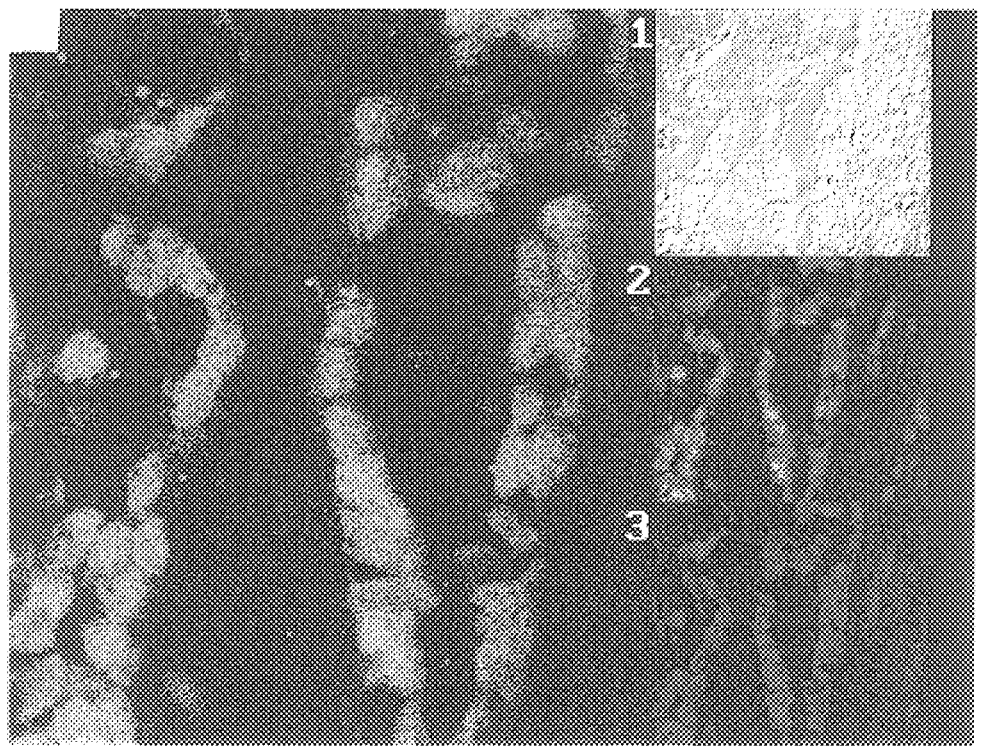
Figure 13C:
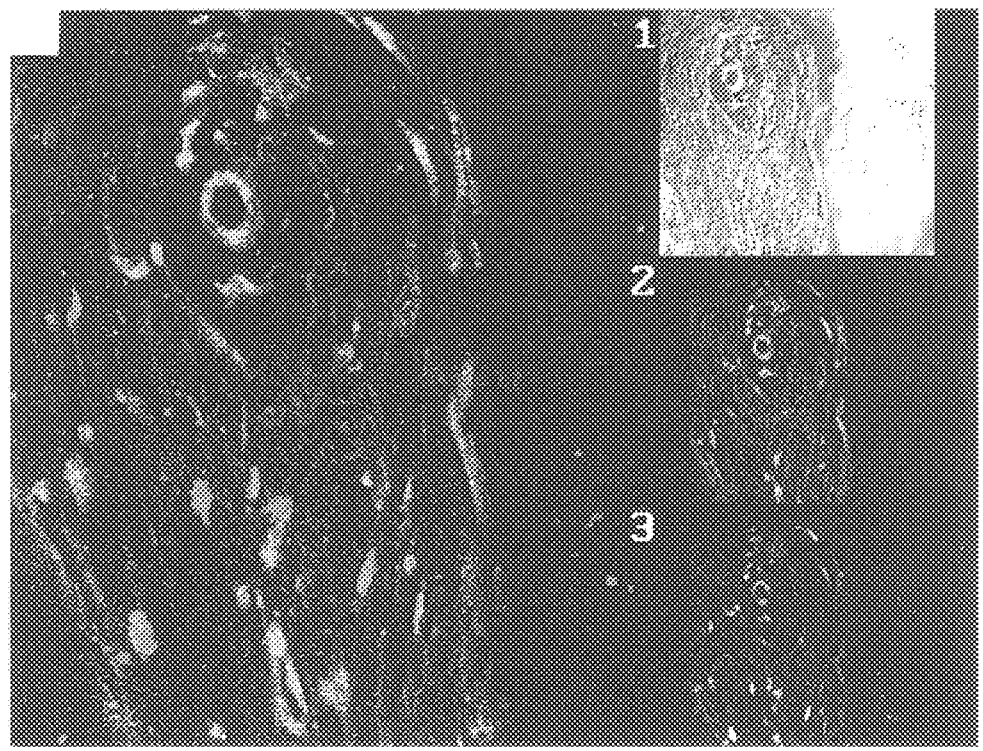
Figure 13D:
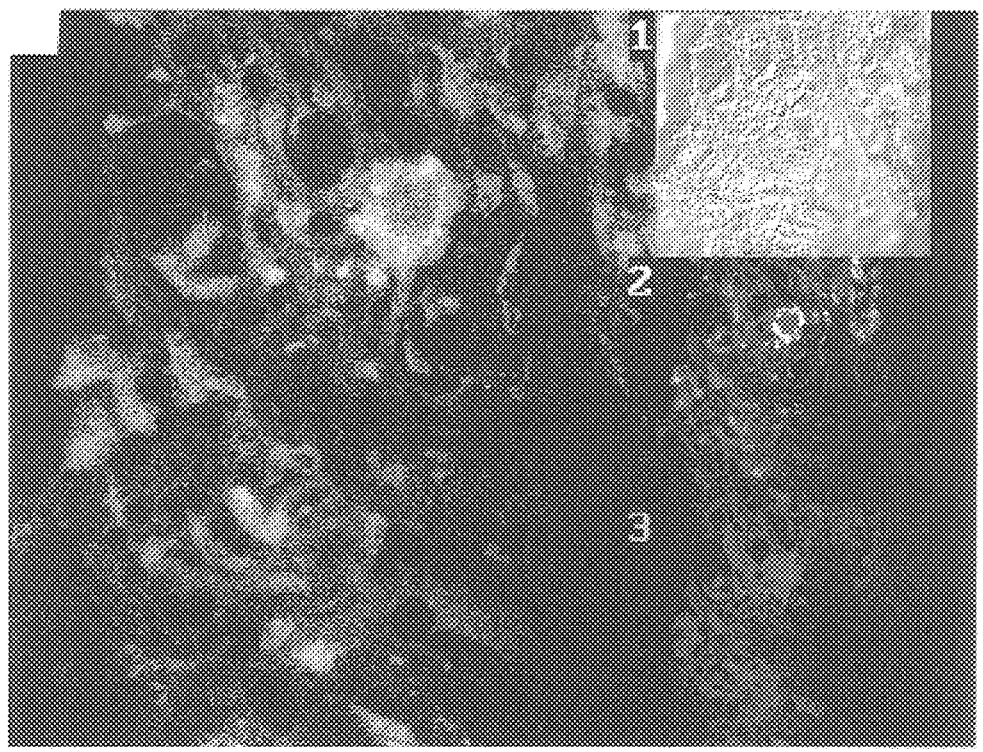

The elevated expression of Met in sarcoma cell lines compared to primary fibroblast cultures and the previous demonstration that NIH/3T3 cells overexpressing Met are tumorigenic (Rong et. al., *Mol. Cell. Biol.* 12: 5152 (1992)) suggested that the high expression of Met may have contributed to the formation of sarcomas in vivo. To explore this possibility, paraffin-embedded human sarcoma sections were stained for Met and HGF/SF, and examined using confocal laser scan microscopy (CLSM). Seven out of eight examined tumors were positive for both Met and HGF/SF staining: one leiomyosarcoma (FIG. 13, part A) and one of two chondrosarcoma examined (the positive tumor is shown in FIG. 13, part B) expressed both Met and HGF/SF, while three osteosarcomas showed significant Met and HGF/SF staining (two tumors are shown; FIGS. 13C and 13D). For each sample, the Nomarski images are presented in panel (1), whereas panels (2) and (3) show the tumor sections stained with anti-Met and anti-HGF/SF antibody, respectively.

In the double-stained overlays (FIGS. 13A–13D), green corresponds to Met staining, red to HGF/SF, and yellow represents co-localization of Met and HGF/SF staining. In each tumor, cells were observed which were positive either for both Met and HGF/SF, or for Met or HGF/SF alone, suggesting that both autocrine and paracrine modes of stimulation can occur. The differential pattern of Met and HGF/SF expression observed in the sarcoma cells suggests heterogeneity in the population of tumor cells which might reflect the state of cell differentiation and/or tumor progression.

These analyses demonstrate that Met overexpression occurs in the primary human sarcomas as well as in sarcoma cell lines (FIG. 21) and therefore, as in the NIH/3T3 model system (Rong et al., *Mol. Cell. Biol.* 12: 5152 (1992)), contribute to the formation of these tumors.

EXAMPLE 7

Autocrine activation of Met in NIH/3T3 cells enhances cell motility, collagenase activity, and invasiveness in vitro, as well as metastasis in vivo Cell lines and antibodies. NIH/3T3 cells transformed with tpr-met, the oncogenic form of met previously described by Park et al. (*Cell* 45: 895 (1986)), were used in these studies and are referred to as "Tpr-Met" cells. These studies also used NIH/3T3 cells transformed by $met^{mu}$ ($Met^{mu}$ cells) or by the coexpression of $met^{hu}$ and $HGF/SF^{hu}$ (HMH cells). (Rong et al., *Mol. Cell. Biol.* 12: 5152 (1992); Rong et al., *Cell Growth & Diff.* 4: 563 (1993)). $Met^{mu}$ and HMH cells are designated as either parental cells, prior to tumor formation in nude mice, or as primary (1°) or secondary (2°) tumor explants. Id. NIH/3T3 cells transformed by ras or src (Kmiecik et al., *Mol. Cell. Biol.* 8: 4541 (1988)) were used as controls. A rare tumorigenic clone of $Met^{hu}$-transfected NIH/3T3 cells (MT cells), transformed by a non-autocrine mechanism, were used as controls for the autocrine-transformed $Met^{mu}$ and HMH cells. (Tsarfaty et al., *Science* 253: 98 (1993)). All cells were maintained as described previously. (Rong et al., *Mol. Cell. Biol.* 12: 5152 (1992); Rong et al., *Cell Growth & Diff.* 4: 563 (1993)).

C28 anti-peptide antibody was raised in rabbits by immunization with the C-terminal 28 amino acids of $Met^{hu}$. (Gonzatti-Haces et al., *Proc. Nat'l. Acad. Sci. U.S.A.* 85: 21 (1988)) The SP260 anti-peptide antibody is a rabbit antiserum directed against the C-terminal 21 amino acids of $Met^{mu}$. (Iyer et al., *Cell Growth & Diff.* 1: 87 (1990). A3.1.2 is a monoclonal antibody against human recombinant HGF (IgG, subclass G2a, a gift from Dr. T. Nakamura, Osaka, Japan).

Immunoprecipitation. The identification of Met and HGF/SF by immunoprecipitation analysis was carried out as described previously. (Rong et al., *Mol. Cell. Biol.* 12: 5152 (1992)). Near-confluent cells were labeled for 6 h with 0.25 mCi of $^{35}$S-methionine and $^{35}$S-cysteine (Translabel, ICN, 1 ml/35-mm dish) in DMEM lacking methionine and cysteine (GIBCO). The labeled cells were lysed in 0.5 ml of RIPA buffer [1% Triton X-100, 1% sodium deoxycholate, 0.1 % sodium dodecylsulfate (SDS), 0.15M NaCl, 0.02M NaPO$_4$ (pH 7.2), 1 mM phenylmethylsulfonyl fluoride (PMSF), 2 mM EDTA, 50 mM NaF, 30 mM sodium pyrophosphate]. Clarified lysates were incubated with the appropriate antibodies at 4° C. overnight. Immune complexes were collected using protein G-Sepharose (GIBCO), and washed twice with RIPA buffer and high-salt buffer (1M NaCl, 10 mM Tris-HCl (pH 7.2) and 0.5% Triton). The complexes were boiled in SDS sample buffer and immunoprecipitates were analyzed by SDS-polyacrylamide gel electrophoresis. The gels were treated with a fluorographic enhancer (Amplify™, Amersham) and exposed to X-ray film (Kodak) with an intensifying screen at −70° C.

In vitro invasiveness assay. Histopathological examination of tumors generated by Met$^{mu}$ and HMH cells revealed that the tumors invaded adjacent tissue. To determine if Met-transformed NIH/3T3 cells displayed invasive activity, Met$^{mu}$ cells and HMH cells were tested in vitro in Boyden chamber basement membrane matrigel assays. Non-transformed NIH/3T3 control cells, Tpr-Met cells, and MT cells also were examined in these studies.

Invasive assays in vitro were performed as described by Albini et al. (*Cancer Res.* 47: 3239 (1989)) using 10-well chemotaxis chambers (NeuroProbe). Lower and upper wells were separated by matrigel-coated (1 μg/mm$^2$, Collaborative Research) Nucleopore filters (8 μm pore size). HGF/SF, when used, was diluted in 0.4 ml DMEM containing 1 mg/ml BSA and placed into the lower well. Cells (10$^5$), in DMEM-BSA were seeded into the upper wells; chambers were incubated overnight at 37° C. Filters were fixed with cold methanol, and stained with Giemsa (Sigma). Noninvading cells on the upper surface of the filter were removed with a cotton swab, while invading cells on lower surface of filters were counted using a light microscope.

In these studies, Met$^{mu}$, HMH and Tpr-Met cells migrated spontaneously through the matrigel-coated filter in the absence of exogenous HGF/SF in the lower chamber, while the MT and NIH/3T3 cells did not migrate (FIG. 14, FIG. 22). When HGF/SF$^{hu}$ was placed in the lower well, the MT cells showed dramatic migration into the membrane, but much less when the mouse ligand was used in the lower well. Marked increase in cell migration also was observed with Met$^{mu}$ cells with either mouse or human HGF/SF in the lower chamber (FIG. 22). These results show that HGF/SF$^{mu}$ has low affinity for Met$^{hu}$, while HGF/SF$^{hu}$ activates both the Met$^{mu}$ and Met$^{hu}$. These results also show that NIH/3T3 cells expressing Met can invade basement membrane matrigel either spontaneously through autocrine stimulation, or in a chemotaxic response, when HGF/SF is placed in the lower well.

There was no significant migration of HMH cells when HGF/SF$^{hu}$, was placed in the lower chamber. However, HMH cells secrete high levels of HGF/SF$^{hu}$. (Rong et al., *Mol. Cell. Biol.* 12: 5152 (1992); Rong et al., *Cell Growth & Diff.* 4: 563 (1993)). Met$^{mu}$ cells, on the other hand, express an excess of receptor over the endogenous ligand (Rong et al., *Cell Growth & Diff.* 4: 563 (1993)) and, therefore, respond to HGF/SF (FIG. 22). Similarly, human soft tissue sarcoma cells express Met$^{hu}$ over the endogenous ligand and can respond mitogenically to HGF/SF$^{hu}$. (Rong et al., *Cancer Research* 53: 5355 (1993)). Tpr-Met cells also display spontaneous migration activity, suggesting that certain signal transduction pathways are shared by the activated oncogene and the autocrine activated receptor. Thus, both autocrine and paracrine Met signalling in mesenchymal cells can promote in vitro invasiveness in the Boyden chamber basement membrane assay. Activation of the Met receptor may induce the motility necessary for this invasive phenotype, but the cells must also synthesize the proteases necessary for penetrating the matrigel.

Collagenase secretion. Both type I and type IV collagenase activity was measured by the method of Nakajima et al., *Cancer Research* 47: 4869 (1987). Aliquots of $^3$H proline-labeled type I or type IV collagen (NEN) were diluted with cold rat tail type I or type IV collagen (Sigma) (8000 cpm/6 μg in 0.5M acetic acid), placed in 96-well plates (Costar) and dried overnight at room temperature in a tissue culture hood. Transfected cells (2×10$^4$ in 200 μl DMEM with 8% calf serum) were added per well and incubated overnight. The supernatant of each well was mixed with 50 μl of ice-cold 10% TCA and 0.5% tannic acid in Eppendorf tubes. After 30 min incubation at 4° C., the mixture was centrifuged and radioactivity in the supernatant was measured by scintillation counting. Collagenase activity was determined by comparison to a known amount of bacterial collagenase (10 U/ml) added to control wells and data are presented as a percentage of the control activity. Each experiment was performed in duplicate and the data is presented as the average of two experiments.

Figure 14A:
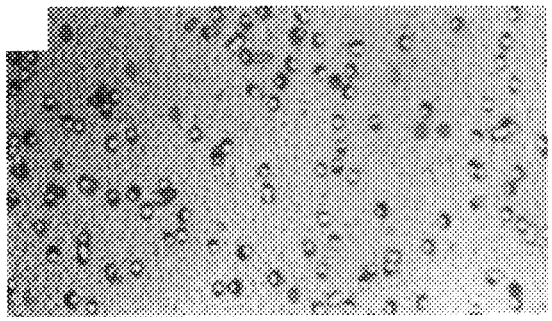
Figure 14B:
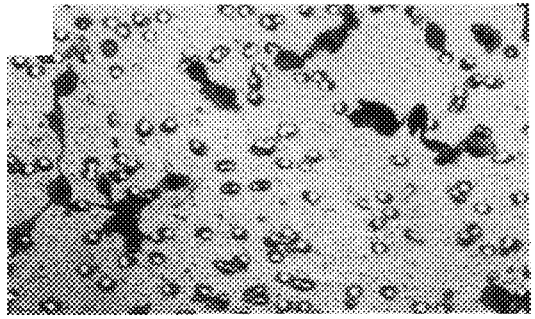
Figure 14C:
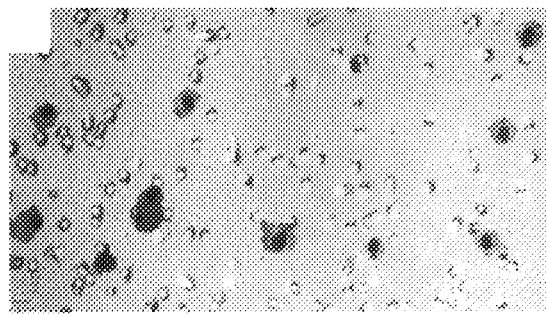
Figure 14D:
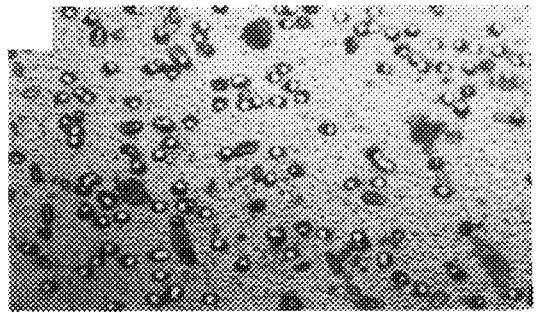
Figure 14E:
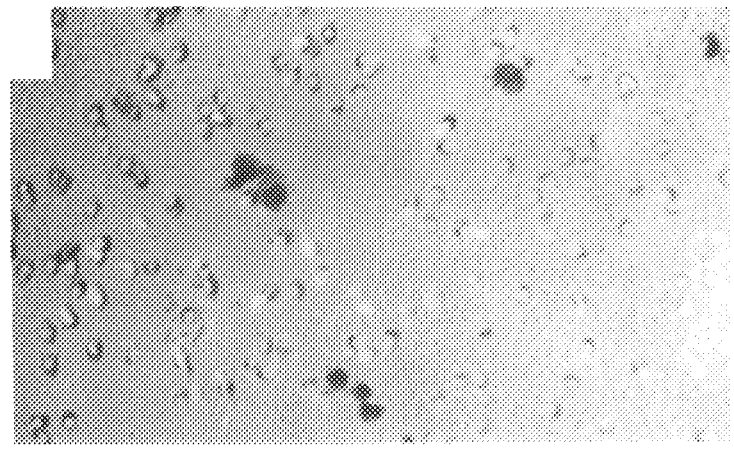
Figure 14F:
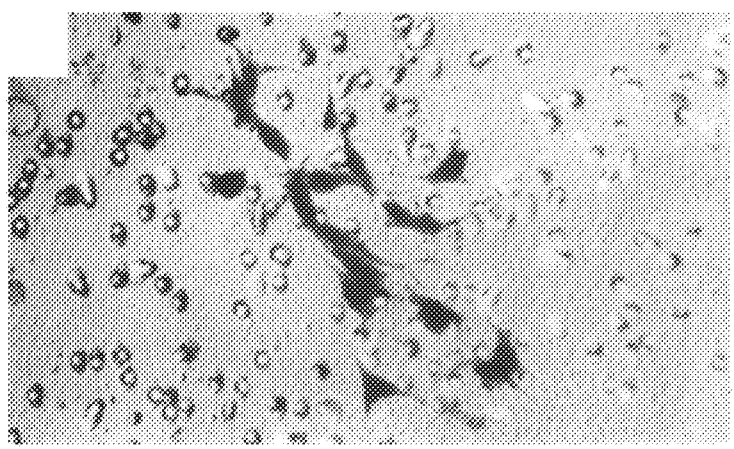

Collagenase activity was examined in parental NIH/3T3 cells, HMH, Met$^{mu}$, MT, and Tpr-Met cells. These analyses showed that enhanced type I and IV collagenase activities were present in HMH, Met$^{mu}$, and Tpr-Met cells (FIG. 15). Comparable results were obtained when the collagenase activity from HMH, Met$^{mu}$, MT, and Tpr-Met cells was determined using denatured collagen. Collagenase activities also were high in the MT tumor cells, even though their invasive activity was stimulated only by exogenous HGF/SF$^{hu}$ (FIGS. 14A and 14B; FIG. 22). These data indicate that increased collagenase secretion may be required for invasiveness, but by itself, is not sufficient to induce the invasive phenotype. The HGF/SF-dependent invasiveness of MT cells must, therefore, be due to enhanced cellular motility and/or induction of other proteases. Furthermore, while the parental HMH cells expressed high levels of collagenase compared to control NIH/3T3 cells, primary and secondary HMH tumor cell explants expressed higher levels (FIG. 15) that correlated with a significant increase in spontaneous in vitro invasiveness (FIG. 14F, FIG. 22).

Experimental metastasis. The tpr-met oncogene, as well as Met-HGF/SF autocrine signaling in NIH/3T3 cells stimulated invasive migration in vitro and protease production (FIGS. 14A–14F and 15; FIG. 22). To determine whether these activities paralleled metastatic activity in vivo, studies were performed to determine whether HMH, Met$^{mu}$, MT and Tpr-Met cells would colonize the lung of nude mice following tall vein injection.

Transfected and G418-selected NIH/3T3, Tpr-Met, Met$^{mu}$, MT, or HMH cells as well as tumor cell explants (10$^6$ cells) were washed twice and resuspended in 0.1 ml of serum-free medium (DMEM, GIBCO). The cells were injected intravenously into the tail vein of weanling athymic mice (Balb/c nu/nu), NFS, Balb/c or triple deficiency mice (NIH-bg-nu-Xid) (Harlan Sprague Dawley, Inc.). When mice showed signs of distress, they were sacrificed and their lungs were removed and processed for histological examination. Briefly, the organs of test mice were immersion fixed in formalin and embedded in paraffin. A 5 μm section was mounted on superfrost slides, stained with hematoxylin and eosin (H&E) and evaluated by light microscopy for identification of metastases. Slides were evaluated blindly, without knowledge of the identity of the injected cells.

Histopathological analyses revealed that parental Met$^{mu}$ cells efficiently induced lung metastases. Parental HMH cells were poorly active in this assay, but primary and secondary tumor cell explants which express much higher levels of Met$^{hu}$ and HGF/SF$^{hu}$ were very efficient at producing lung tumors. Moreover, explanted lung tumor cells generated by injection of primary HMH tumor cells, exhibit increased levels of Met$^{hu}$ and HGF/SF$^{hu}$ (FIGS. 16A and 16B, lanes 3–6), similar to the enhanced levels of expression found in secondary tumor explants in nude mouse tumor assays. (Rong et al., *Cell Growth & Diff.* 4: 563 (1993)). Met also was abundantly expressed in lung tumor cell explants, generated by injection of parental Met$^{mu}$ cells (FIG. 16C, lanes 1 and 2). Interestingly, two of the animals injected with Neo$^r$ NIH/3T3 control cells developed lung tumors. These tumors, like the Met$^{mu}$ tumors, expressed high levels of endogenous Met$^{mu}$ (FIG. 16C, lanes 4 and 5).

Amplification of endogenous Met occurs frequently in spontaneous NIH/3T3 cell transformants (Cooper et al., *Nature* 311: 29 (1984); Hudziak et al., *Cell Growth & Diff.* 1: 129 (1990)) and Met$^{hu}$ is also amplified in human sarcomas (Rong et al., *Cancer Research* 53: 5355–5360 (1993)). The present studies show that spontaneous Met$^{mu}$ amplification is associated with experimental metastasis. The Tpr-Met cells also were very efficient at populating the lung, while MT cells which are tumorigenic in nude mice, did not efficiently colonize the lung (FIG. 23, part A).

HMH, Met$^{mu}$, and Tpr-Met cells also were injected into the tail vein of immune competent Balb/c and NFS mice, as well as into triple immunodeficient mice (FIG. 23, part B). As observed with nude mice, HMH, Met$^{mu}$, and Tpr-Met-transformed cells colonized the lung of triple immunodeficient animals; but only the Tpr-Met cells established tumors in the lung of the immune competent animals (FIG. 23, part B). It is not clear how the tpr-met oncogene can induce tumors that evade recognition in immune intact animals.

Spontaneous metastasis. Various met-transformed NIH/3T3 cells were tested for spontaneous metastasis activity in nude mice. In these studies, transfected and G418-selected NIH/3T3, Tpr-Met, Met$^{mu}$, MT or HMH cells, as well as their tumor cell explant cells ($10^6$, and $10^5$, cells, respectively), were washed twice and resuspended in 0.1 ml of serum-free medium (DMEM, GIBCO). The cells were injected subcutaneously into the back of athymic mice (Balb/c nu/nu, Harlan Sprague Dawley, Inc.). Tumor formation was monitored twice weekly. Fast-growing tumors at the site of inoculation (15–20 mm in size) were surgically removed and when the animals appeared distressed, they were sacrificed and major organs (lung, liver, spleen, kidney, stomach, colon, brain and skin) were examined as described above for the development of metastases.

Spontaneous metastasis assays also were performed by injecting $4 \times 10^5$ cells into the mammary fat pad. (Leone et al., *Oncogene* 8: 2325 (1993)). When mice appeared distressed, the animals were sacrificed and their lungs were analyzed for metastasis.

Figure 17A:
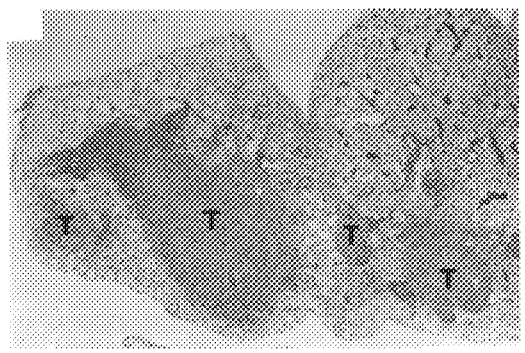
Figure 17B:
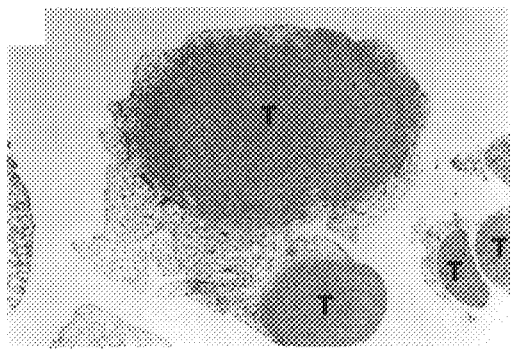
Figure 17C:
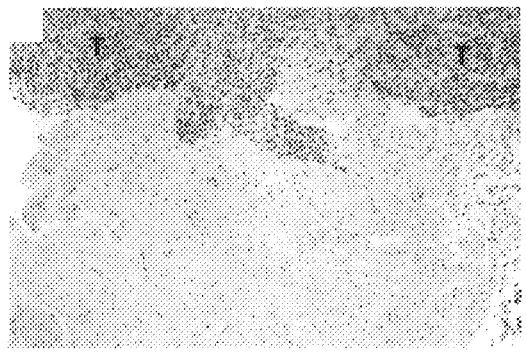
Figure 17D:
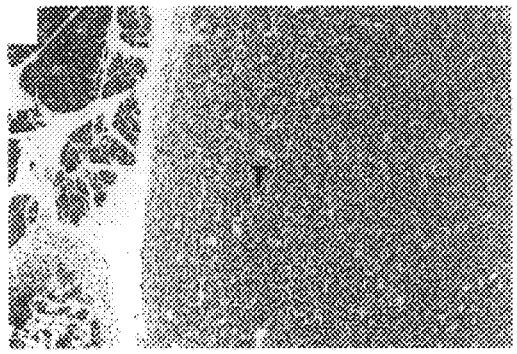
Figure 17E:
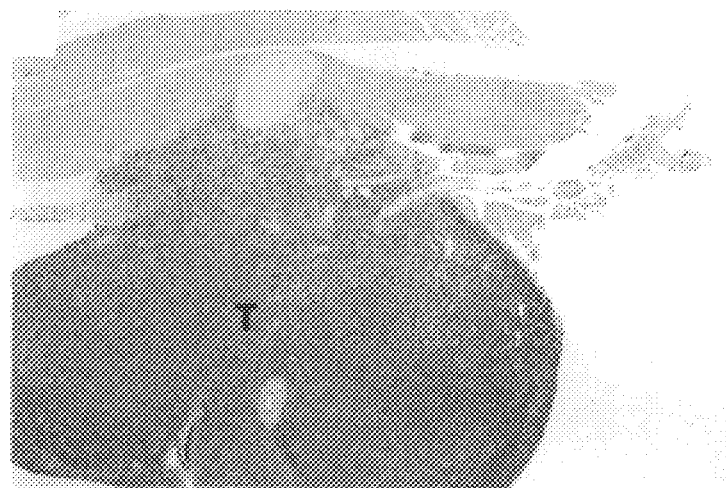
Figure 17F:
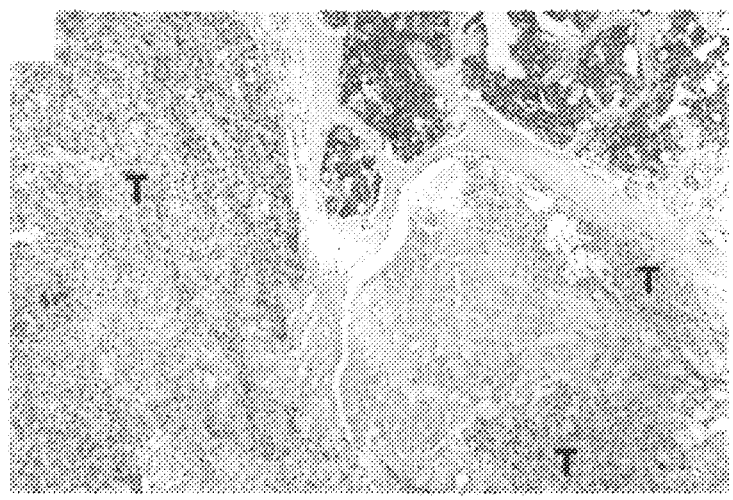

In these studies, NIH/3T3 cells transformed by activated ras or src oncogenes served as positive controls since these cells efficiently generate lung metastases (FIG. 24). (Chambers et al., *Mol. Cell. Biol.* 5: 728 (1985); Egan et al., *Mol. Cell. Biol.* 7: 830 (1985); Hill et al., *Nat'l. Can. Inst.* 80: 484 (1988); Creig et al., *Proc. Nat'l. Acad. Sci. U.S.A.* 2: 3698 (1985); Thorgeirsson et al., *Mol. Cell. Biol.* 5: 259 (1985); Bradley et al., *Proc. Nat'l. Acad. Sci. U.S.A.* 83: 5277 (1986)). Multifocal, lung metastases were observed in mice injected with Tpr-Met, HMH and Met$^{mu}$ cells and the primary tumor cell explants (FIG. 24, part A; FIGS. 17A and 17B) showed greatly enhanced metastatic activity. Interestingly, at low cell inoculation densities, the Met$^{mu}$ cells metastasized to the parotid and sublingual salivary gland and obliterated the entire submandibular gland (FIG. 17D). These cells also metastasized to the retroperitoneum (FIG. 17F), while HMH cells colonized and invaded both the heart (FIG. 17C) and the diaphragm (FIG. 17E). In contrast, the MT cells did not produce metastases in subcutaneous assays.

HMH, Met$^{mu}$, and Tpr-Met cells also were tested for metastatic activity after inoculating the cells into the mammary fat pad of nude mice. All three cell types induced spontaneous lung metastases (FIG. 24, part B) and, again, the tumor cell passages (primary and tertiary) were much more active in this assay. These results demonstrate that Met-HGF/SF autocrine expression in NIH/3T3 cells induces experimental and spontaneous metastasis in vivo.

Thus, the studies of Example 7 demonstrate that the level of Met and HGF/SF expressed in NIH/3T3 cells directly correlates with invasiveness activity in vitro, the expression of collagenase activity, as well as enhanced activity in both experimental and spontaneous metastases. Also, tumor cell explants from nude mice have markedly increased autocrine Met activation concomitant with enhanced activity in experimental and spontaneous metastasis assays in vivo.

EXAMPLE 8

A comparison of the expression of HGF/SF in NIH/3T3 mouse fibroblast cells transfected with DNA encoding HFG/SF with HGF/SF expression in the same cells with DNA encoding Met:HGF/SF The NIH/3T3 cells were metabolically labeled with Translabel (ICN) for 5 hours. The supernatants were concentrated 7- to 8-fold using a centricon apparatus (molecular weight cut off of 10,000, Amicon). The volumes were adjusted to 0.3 ml with RIPA buffer and immunoprecipitated with HGF/SF$^{hu}$ monoclonal antibody A3.1.2, FIG. 18, parts A and B. In FIG. 18, part B, aliquots of the samples were reimmunoprecipitated with HGF/SF$^{hu}$ rabbit anti-serum anti-rhHGF. In FIG. 18, part A, lanes 1 and 3, shows HGF/SF expression in two independent NIH/3T3 parental cell lines transfected with met$^{hu}$, and HGF/SF cDNAs; lane 2, shows HGF/SF expression levels in tumor explants derived from the parental cells tested in lane 1. Lanes 4 and 5, show expression levels from two independent primary tumor explants that were derived from parental cells tested in lane 3. Lane 6, shows expression in NIH/3T3 fibroblast control cells. Lane 7, represents HGF/SF expression in NIH/3T3 parental cells transfected with HGF/SF$^{hu}$. Lanes 8–10, show HGF/SF expression from four independent primary tumor explants derived and described in Rong et al. , *Mol. Cell. Biol.*, 12: 5152 (1992) from the HGF/SF$^{hu}$ transfected parental cells tested in lane 7. In FIG. 18, part B, lane 1, shows HGF/SF expression in NIH/3T3 cells transfected with met$^{hu}$ and HGF/SF$^{hu}$ cDNAs; lane 2, tumor explant derived from cells tested in lane 1; lane 3, NIH/3T3 cells. Lanes 4 and 5 show HGF/SF expression in two independent tumor explants of HGF/SF transfected parental cells analyzed in FIG. 18, part A, lane 7.

FIG. 18 shows that HGF/SF is only amplified in tumors when Met is present. Compared to parental NIH/3T3 cells with transfected met and HGF/SF cDNAs (FIG. 18, part A, lanes 1 and 3), significant increases in HGF/SF production occur after tumorigenesis in tumor explant cells (FIG. 18, part A, lanes 2, 4 and 5). The three isotopically-labeled protein bands represent p87 (HGF/SF uncleaved), p68α and p34β (cleaved subunits). By contrast, the dramatic amplification of HGF/SF does not occur in tumor explants when HGF/SF is present in NIH/3T3 cells without Met (FIG. 18, part A, c.f. lane 7 to lanes 8–11).

EXAMPLE 9

Expression of HFG/SF in human and mouse transfected cells

Figure 19B:
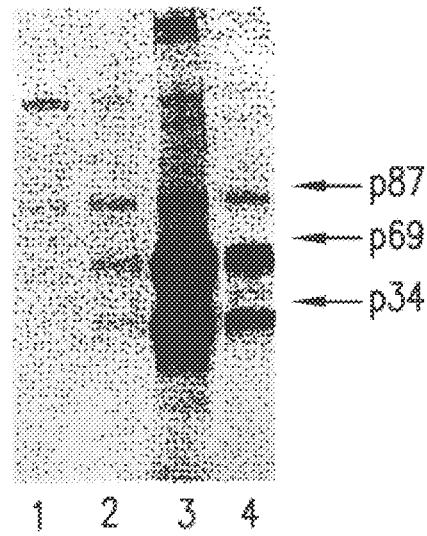

Met$^{mu}$ (FIG. 19, part A) or Met$^{hu}$ (FIG. 19, part B) expressing cells were transfected with LTR-HGF/SF$^{hu}$ cDNA (Rong et al., *Mol. Cell. Biol.* 12: 5152 (1992)), a selectable marker plasmid (Neo for SK-LMS-1, HyGro for C127-Met$^{mu}$) and were grown in selective media as a pool of cells or as individual clones. After selection, the cells were labeled for 14 hours with Trans $^{35}$S-label and the supernatant was immunoprecipitated with a HGF$^{hu}$ polyclonal antisera (R&D Systems) and protein G agarose. The immunoprecipates were separated by SDS-PAGE on a 4–15% gel. The gel was subsequently fixed, incubated with fluorographic reagent, dried and exposed to x-ray film. FIG. 19, part A shows HGF/SF$^{hu}$ expression in C127 Met$^{mu}$ mouse cells. Lane 1, a pool of cells transfected with HGF/SF$^{hu}$ expression in SK-LMS-1 human leiomyosarcoma cells. Lane 1, a pool of cells transfected with neo$^r$ gene only; lane 2, a pool of cells transfected with HGF/SF$^{hu}$; lanes 3 and 4, clones of cells transfected with HGF/SF$^{hu}$.

EXAMPLE 10

HGF/SF is overexpressed in C127 Met$^{mu}$ producing cells and induces tumorigenesis in athymic nude mice Parental C127 mouse cells (ATCC #CRL1616) have very low levels of Met$^{mu}$ but do not express HGF/SF$^{mu}$ and are not tumorigenic in nude mice. C127 cells were transfected with murine LTR-met$^{mu}$ cDNA, a construct described in Rong et al., *Mol. Cell. Biol.* 12: 5152 1992), and cell clones were identified that express high levels of Met$^{mu}$ (data not shown). When C127 cells expressing high levels of Met$^{mu}$ are super-transfected with LTR-HGF/SF$^{hu}$ cDNA, they express high levels of HGF/SF (FIG. 19A, lanes 1, 2, 3, and 4), are morphologically transformed and they become highly tumorigenic in athymic nude mice (tumors in ~2–3 weeks). Thus, in a totally different cell system, high levels of HGF/SF can be produced, when Met is overexpressed.

EXAMPLE 11

HGF/SF$^{hu}$ is overexpressed in SK-LMS-1 Met$^{hu}$ producing cells: Growth of human tumor cells in athymic nude mice SK-LMS-1 cells (ATCC #HTB88), a human cell line established from a leiomyosarcoma tumor, expresses high levels of Met$^{hu}$, but very low levels of endogenous HGF/SF$^{hu}$ (FIG. 19, part B, lane 1) (Rong et al., *Cancer Res.* 53:5355 (1993). When LTR-HGF/SF$^{hu}$ cDNA is transfected into SK-LMS-1 they express high levels of HGF/SF and the cells become highly tumorigenic in nude mice (FIG. 19, part B, lanes 2–4; Table 5, below). This demonstrates, in yet another mesenchymal system, that HGF/SF is overexpressed when cells express high levels of Met.

Applicants discovered that Met down-regulates endogenous HGF/SF expression. It is only by ectopic expression from an LTR that there is ligand overexpression. In three primary human fibroblast cell lines examined, HGF/SF is high, Met$^{hu}$ is very low (Rong et al., *Cancer Res.* 53:5355 (1993)). In almost all human mesenchymal tumor cell lines examined, Met$^{hu}$ expression is high and HGF/SF$^{hu}$ is low (Rong et al., *Cancer Res.* 53: 5355 (1993). Applicants have shown that by transfection of LTR-hHGF/SF cDNA into SK-LMS-1 cells, this human mesenchymal tumor cell line then expresses high levels of HGF/SF. Applicants further discovered that these cells grow in athymic nude mice, whereas non-transfected cells do not. This observation has led to yet another invention directed to a method of making or improving the success of growing human tumor cell xenographs in athymic nude mice, as described above.

TABLE 5

Effect of HGF/SF Expression on SK-LMS-1 Tumorigenicity in Athymic Nude Mice

|  | Mouse with tumor/total mice | Number of cells injected | Latency (weeks) |
| --- | --- | --- | --- |
| neo$^r$ | 0/1 | 2 × 10$^6$ | — |
| neo$^r$HGF/SF$^{hu}$ | 6/6 | 2 × 10$^6$ | 3.5 |
| neo$^r$ | 0/3 | 4 × 10$^5$ | — |
| neo$^r$ | 4/6 | 4 × 10$^5$ | 4.5 |

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A method of producing human Hepatocyte Growth Factor/Scatter Factor (HGF/SF$^{hu}$) comprising the steps of:

(a) transfecting mammalian cells with DNA encoding HGF/SF$^{hu}$ and a met protooncogene protein (Met) operatively linked to a control sequence which allows expression of said HGF/SF$^{hu}$ and said Met;

(b) introducing cells transfected in accordance with step (a) into an immunocompromised mouse, thereby generating a primary tumor;

(c) explanting and propagating cells of said primary tumor in vitro;

(d) selecting those cells propagated in accordance with step (c) which express levels of HGF/SF$^{hu}$ and levels of Met which are higher than the levels of HGF/SF$^{hu}$ and Met expressed in a similar transfected mammalian cell prior to being introduced into the immunocompromised mouse;

(e) introducing cells selected in accordance with step (d) into a mouse, thereby producing a secondary tumor;

(f) explanting and propagating cells of said secondary tumor in vitro; and (g) isolating HGF/SF$^{hu}$ produced by said cells of step (f).

2. A method of producing human Hepatocyte Growth Factor/Scatter Factor (HGF/SF$^{hu}$) comprising the steps of:

(a) transfecting NIH/3T3 cells with DNA encoding HGF/SF$^{hu}$ and a met protooncogene protein (Met) operatively linked to a control sequence which allows expression of said HGF/SF$^{hu}$ and said Met;

(b) introducing cells transfected in accordance with step (a) into an immunocompromised mouse, thereby generating a primary tumor;

(c) explanting and propagating cells of said primary tumor in vitro;

(d) selecting those cells propagated in accordance with step (c) which express levels of HGF/SF$^{hu}$ and levels of Met which are higher than the levels of HGF/SF$^{hu}$ and Met expressed in a similar transfected mammalian cell prior to being introduced into the immunocompromised mouse;

(e) introducing cells selected in accordance with step (d) into a mouse, thereby producing a secondary tumor;

(f) explanting and propagating cells of said secondary tumor in vitro; and (g) isolating HGF/SF$^{hu}$ produced by said cells of step (f).

3. A method of producing human Hepatocyte Growth Factor/Scatter Factor (HGF/SF$^{hu}$) comprising the steps of:

(a) co-transfecting mammalian cells with a first DNA encoding HGF/SF$^{hu}$ operatively linked to a control sequence which allows expression of said HGF/SF$^{hu}$ and a second DNA encoding a met protooncogene protein (Met) operatively linked to a control sequence which allows expression of said Met;

(b) introducing cells co-transfected in accordance with stop (a) into an immunocompromised mouse, thereby generating a primary tumor;

(c) explanting and propagating cells of said primary tumor in vitro;

(d) selecting those cells propagated in accordance with step (c) which express levels of HGF/SF$^{hu}$ and levels of Met which are higher than the levels of HGF/SF$^{hu}$ and Met expressed in a similar co-transfected mammalian cell prior to being introduced into the immunocompromised mouse;

(e) introducing cells selected in accordance with step (d) into a mouse, thereby producing a secondary tumor;

(f) explanting and propagating cells of said secondary tumor in vitro; and (g) isolating HGF/SF$^{hu}$ produced by said cells of step (f).

4. A method of producing human Hepatocyte Growth Factor/Scatter Factor (HGF/SF$^{hu}$) comprising the steps of:

(a) co-transfecting NIH/3T3 cells with a first DNA encoding HGF/SF$^{hu}$ operatively linked to a control sequence which allows expression of said HGF/SF$^{hu}$ and a second DNA encoding a met protooncogene protein (Met) operatively linked to a control sequence which allows expression of said Met;

(b) introducing cells co-transfected in accordance with step (a) into an immunocompromised mouse, thereby generating a primary tumor;

(c) explanting and propagating cells of said primary tumor in vitro;

(d) selecting those cells propagated in accordance with step (c) which express levels of HGF/SF$^{hu}$ and levels of Met which are higher than the levels of HGF/SF$^{hu}$ and Met expressed in a similar co-transfected mammalian cell prior to being introduced into the immunocompromised mouse;

(e) introducing cells selected in accordance with step (d) into a mouse, thereby producing a secondary tumor;

(f) explanting and propagating cells of said secondary tumor in vitro; and (g) isolating HGF/SF$^{hu}$ produced by said cells of step (f).

5. The method of claim 1, wherein the transfected cells are introduced into the immunocompromised mouse by injection.

6. The method of claim 1, wherein the met protooncogene protein is a human met protooncogene protein.

7. The method of claim 1, wherein the met protooncogene protein is a mouse met protooncogene protein.

8. The method of claim 2, wherein the transfected cells are introduced into the immunocompromised mouse by injection.

9. The method of claim 2, wherein the met protooncogene protein is a human met protooncogene protein.

10. The method of claim 2, wherein the met protooncogene protein is a mouse met protooncogene protein.

11. A mammalian cell line co-transfected with a first DNA vector comprising, in operable linkage, a promoter from a long terminal repeat of a retrovirus, DNA encoding the entire coding domain of Met protooncogene protein and a polyadenylation signal, and a second DNA vector comprising, in operable linkage, a promoter from a long terminal repeat of a retrovirus, DNA encoding human Hepatocyte Growth Factor/Scatter Factor (HGF/SF$^{hu}$) and a polyadenylation signal, wherein said co-transfection results in expression of said Met protooncogene protein and said HGF/SF$^{hu}$.

12. A mammalian cell line transfected with a DNA vector comprising, a DNA sequence encoding the entire coding domain of Met protooncogene protein operatively linked to a promoter and a polyadenylation signal, and a DNA sequence encoding human Hepatocyte Growth Factor/ Scatter Factor (HGF/SF$^{hu}$) operatively linked to a promoter and a polyadenylation signal, wherein said transfection results in expression of said Met protooncogene protein and said HGF/SF$^{hu}$.

* * * * *